United States Patent
Nakano et al.

(10) Patent No.: US 11,285,235 B2
(45) Date of Patent: Mar. 29, 2022

(54) AROMA DISPLAY

(71) Applicant: AROMAJOIN CORPORATION, Kyoto (JP)

(72) Inventors: Kazuhiro Nakano, Kyoto (JP); Quang Van Nguyen, Kyoto (JP); Dong Wook Kim, Kyoto (JP)

(73) Assignee: AROMAJOIN CORPORATION, Kyoto (JP)

( * ) Notice: Subject to any disclaimer, the term of this patent is extended or adjusted under 35 U.S.C. 154(b) by 0 days.

(21) Appl. No.: 17/090,935

(22) Filed: Nov. 6, 2020

(65) Prior Publication Data

US 2021/0138101 A1    May 13, 2021

(30) Foreign Application Priority Data

Nov. 12, 2019  (JP) .............................. JP2019-204857

(51) Int. Cl.
*A61L 9/12*    (2006.01)

(52) U.S. Cl.
CPC ............... *A61L 9/125* (2013.01); *A61L 9/122* (2013.01); *A61L 2209/133* (2013.01); *A61L 2209/134* (2013.01)

(58) Field of Classification Search
None
See application file for complete search history.

(56) References Cited

U.S. PATENT DOCUMENTS

| 2011/0253800 | A1* | 10/2011 | Doty | ........................ A61L 9/122 239/34 |
|---|---|---|---|---|
| 2015/0283282 | A1 | 10/2015 | Kim et al. | |
| 2018/0028709 | A1 | 2/2018 | Fujita et al. | |
| 2018/0071425 | A1 | 3/2018 | Jin et al. | |
| 2018/0169288 | A1 | 6/2018 | Kelsen | |
| 2018/0369442 | A1 | 12/2018 | Kelsen | |
| 2019/0160195 | A1 | 5/2019 | Kelsen | |

FOREIGN PATENT DOCUMENTS

| JP | 2014-092673 A | 5/2014 |
|---|---|---|
| JP | 2014-092674 A | 5/2014 |
| JP | 2018-516719 A | 6/2018 |
| JP | 2018-527039 A | 9/2018 |
| WO | 2016/143188 A1 | 9/2016 |
| WO | 2018/091766 A1 | 5/2018 |

* cited by examiner

*Primary Examiner* — Jelitza M Perez
(74) *Attorney, Agent, or Firm* — Keating and Bennett, LLP

(57) ABSTRACT

An aroma display includes a housing 64 accommodating aroma cartridges 180 to 214 and a cap having an opening for emitting scented air. The cartridge includes a housing having a hollow portion and an upper surface and a scent source held therein. The housing has air-feeding inlets and a scent-emitting opening for externally emitting scented air, and an air-feeding mechanism for feeding air to the air-feeding inlet of the selected cartridge is provided. The housing 64 has an outer cartridge-loading section and an inner cartridge-loading section, the outer cartridge-loading section accommodates outer cartridges such that the distance between the geometrical center of each cartridge and the central axis becomes a first distance, and the inner loading section accommodates the inner cartridges such that the distance between the geometrical center of each cartridge and the central axis becomes smaller than the first distance.

12 Claims, 15 Drawing Sheets

AROMA DISPLAY

CROSS-REFERENCE TO RELATED APPLICATION

This non-provisional application claims priority under 35 U.S.C. § 119(a) to Patent Application 2019-204857 filed in Japan on Nov. 12, 2019, the entire contents of which are hereby incorporated by reference.

BACKGROUND OF THE INVENTION

Field of the Invention

The present invention relates to an aroma display and, more specifically, to an improvement of an aroma display that is capable of emission of various scents by loading a plurality of aroma cartridges.

Description of the Related Art

Human communication is done in various modalities based on human senses. Most frequently used are visual and auditory modes. By contrast, olfaction or sense of smell, on which we rely considerably in our lives, is hardly used for communication. If the sense of smell can be utilized in addition to visual and auditory senses, communication would be more effective and various people would be able to share their experiences more profoundly.

Focusing on this point, recently, devices have been used which are used with audio-visual-reproducing devices such as television receivers, personal computers, and game machines for generating scents appropriate for the scenes. In the present Specification, such a device that generates scents appropriate for scenes will be referred to as an aroma display.

Without the capability to freely switch from one scent to another, an aroma display cannot make full use of scents. For this purpose, one possible approach is to prepare a plurality of cartridges (referred to as aroma cartridges) each containing a pre-selected scent emission source (referred to as a scent source), to load them in an aroma display, and to cause the desired cartridge to emit the scent. Such an aroma display is disclosed in US2015/0283282.

According to the disclosure of US2015/0283282, a hollow aroma cartridge is prepared and a scent source is sealed in the hollow portion. A scent channel is formed for emitting the scent from the scent source inside. An air-feeding mechanism for feeding air to the hollow portion of the aroma cartridge at a desired timing is provided on the side of the aroma display. As a result, pressure in the hollow portion becomes higher and a scent is emitted from the aroma cartridge to the inside of the aroma display through the scent passage. This scent is guided through a space between a housing and a cap of the aroma display to an opening portion or an opening nearby provided at the center of the cap, and the scent is emitted from the aroma display through the opening portion or the opening.

Separate from these air-feeding mechanisms for emitting scent from the cartridge, an air passage leading to the opening portion of the cap is provided, and at its bottom, a mechanism for emitting a scent-free air is provided. The air from the air-emitting mechanism flows near the outlet of the scent passage of the aroma display to the said opening portion. After emitting a scent, when one wishes to switch to another scent, scent-free air is emitted from the air-emitting mechanism to blow away the scented air and thereafter, the next scent is emitted. At this time, if scent-free air from the air-emitting mechanism is also emitted, the scent from the aroma display is emitted through the air to the outside of the opening portion of the cap. Therefore, scents can be switched at a desired timing without undesirable mixing of scents, and the scent can be carried far and wide.

By the aroma display having the above-described structure, scents can freely be switched by selecting which air-feeding mechanism is to be operated. Further, by operating the air-emitting mechanism for emitting scent-free air at that time, undesirable blending of scents can be prevented. Which air-feeding mechanism is to be operated at which timing can be controlled by sending external commands to the aroma display. Therefore, the aroma display can achieve magnificent effects of emitting desired scents appropriately by causing desired air-feeding mechanisms to operate at desired timings of movies or animated films.

In order to increase the types of scents that can be generated by the aroma display disclosed in US2015/0283282, the number of aroma cartridges loadable to the aroma display may be increased. In the aroma display disclosed in US2015/0283282, however, aroma cartridges are arranged in a circle around the central axis. Therefore, if the number of loadable cartridges is increased, the housing of the aroma display becomes larger. Though this increase in size of the housing can be prevented by shrinking the size of each aroma cartridge, the compatibility of aroma cartridges with other aroma displays will be lost, which is disadvantageous.

Assume, for example, that a user who has been using an aroma display allowing use of a certain number of aroma cartridges buys a new aroma display that allows use of a larger number of aroma cartridges. In such a case, the user naturally thinks that his/her aroma cartridges used in the past are also usable in the new aroma display. If his/her old aroma cartridges are not compatible with the new aroma display, the user has to buy a large number of new aroma cartridges.

BRIEF SUMMARY OF THE INVENTION

Therefore, an object of the present invention is to provide an aroma display that can emit a desired scent or scents using a large number of aroma cartridges while preventing increase in size of the housing, without using any special aroma cartridges other than common aroma cartridges.

According to a first aspect, the present invention provides an aroma display for emitting scented air from a desired aroma cartridge of a plurality of aroma cartridges each having a scent source sealed therein, including: an aroma-cartridge-accommodating housing for accommodating the plurality of aroma cartridges around a first axis; and a cap attached to the aroma-cartridge-accommodating housing to cover the aroma-cartridge-accommodating housing, having an opening through which the scented air is emitted. Each of the plurality of aroma cartridges has a housing with a hollow portion and a first surface, and a scent source sealed in the hollow portion, the housing having an air-feeding inlet for feeding air to the hollow portion, and a scent-emitting opening for emitting scented air from the scent source to the outside of the housing in response to increase of pressure in the hollow portion caused by the air fed from the air-feeding inlet, the scent-emitting opening formed at a position on the first surface of the geometrical center of the first surface. The aroma display further includes: an air-feeding mechanism for individually feeding air to the air-feeding inlet of the plurality of aroma cartridges. The aroma-cartridge-accommodating housing includes a first cartridge-loading section allowing loading of a first group of aroma cartridges consisting of a first number of aroma cartridges and a second cartridge-loading section allowing loading of a second group of aroma cartridges consisting of a second number of aroma cartridges, the second number being equal to or smaller than the first number. The first cartridge-loading section allows loading of the aroma cartridges of the first group such that a distance between the geometrical center of each aroma cartridge of the first group and the first axis becomes a first distance. The second cartridge-loading section allows loading of the aroma cartridges of the second group such that a distance between the geometrical center of each aroma cartridge of the second group and the first axis becomes a second distance smaller than the first distance.

Preferably, the first cartridge-loading section accommodates the aroma cartridges of the first group such that the first surfaces of aroma cartridges of the first group are positioned on a first common plane.

More preferably, the second cartridge-loading section accommodates the aroma cartridges of the second group such that the first surfaces of aroma cartridges of the second group are positioned on a second common plane.

Further preferably, the first common plane is the same as the second common plane.

Preferably, the first cartridge-loading section accommodates the aroma cartridges of the first group such that a distance between an opening on the first surface of the aroma cartridges of the first group and the first axis becomes a third distance smaller than the first distance.

More preferably, the second cartridge-loading section accommodates the aroma cartridges of the second group such that a distance between an opening on the first surface of the aroma cartridges of the second group and the first axis becomes a fourth distance larger than the second distance and smaller than the first distance.

More preferably, the fourth distance is equal to or larger than the third distance.

Preferably, the absolute value of difference between the third and fourth distances is equal to or smaller than 10% of the fourth distance.

More preferably, the absolute value of difference between the third and fourth distances is equal to or smaller than 5% of the fourth distance.

More preferably, the aroma display further includes a plurality of tubes respectively connecting the scent-emitting opening of the plurality of aroma cartridges and the opening of the cap.

Preferably, among the plurality of tubes, each of the tubes of a first group corresponding to the aroma cartridges of the first group has a first end in contact with the scent-emitting opening of the aroma cartridge and a second end opened in the opening of the cap. The cap holds the tubes of the first group such that each of the second ends of the tubes of the first group is positioned in a first circle on a plane perpendicular to the first axis.

More preferably, among the plurality of tubes, each of the tubes of a second group corresponding to the aroma cartridges of the second group has a first end in contact with the scent-emitting opening of the aroma cartridge and a second end opened in the opening of the cap. The cap holds the tubes of the second group such that each of the second ends of the tubes of the second group is positioned in a second circle on a plane perpendicular to the first axis.

Further preferably, the ratio of the number of aroma cartridges of the first group to the number of aroma cartridges of the second group is M:N (where M, N are relatively prime natural numbers satisfying the relation M>N). The cap includes a cover having an end portion fixed on a circumferential wall at an end portion of the aroma-cartridge-accommodating housing on the side of the cap and the opening formed at the center, and having a shape gradually tapered upward from the end portion to the opening, and a plurality of tube fixings each for detachably fixing the M tubes of the first group and the N tubes of the second group on a surface of the cover on the side of the aroma-cartridge-accommodating housing.

Preferably, the first and second circles are on mutually-different planes.

More preferably, the aroma display further includes an air-emitting mechanism provided on a side opposite to the cap with respect to the aroma-cartridge-accommodating housing, for feeding scent-free air to the opening of the cap.

More preferably, the aroma display further includes a duct member provided passing through the central portion of the aroma-cartridge-accommodating housing to surround the first axis, for guiding wind fed from the air-emitting mechanism to the opening of the cap. The cap includes a nozzle having a bottom portion in contact with an end portion on the side of the cap of the duct member and a tip end portion of a smaller area than the bottom portion, defining circumference of the opening. The second end of each of the plurality of tubes opens to the inside of a space defined by the nozzle.

Preferably, the aroma display further includes an air-emitting mechanism provided on a side opposite to the cap with respect to the aroma-cartridge-accommodating housing, for feeding scent-free air to the opening of the cap.

More preferably, the housing of the plurality of aroma cartridges has a triangular prism shape, and the first surface is an upper surface of the triangular prism.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
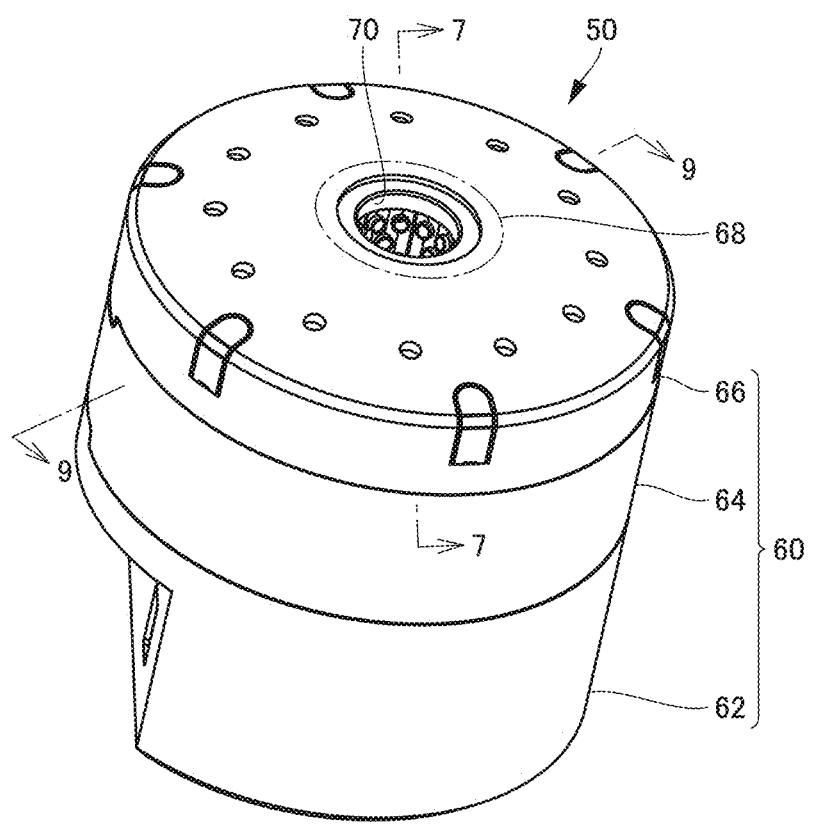
FIG. 1 shows an appearance of an aroma display in accordance with a first embodiment of the present invention.

In the following description and in the drawings, the same components are denoted by the same reference characters. Therefore, detailed description thereof will not be repeated. Further, not all the parts of the embodiments described below are essential to the implementation of the present invention. The components essential to the implementation of the present invention will be defined by the claims.

First Embodiment

<Structure>

FIG. 1 shows an appearance of an aroma display 50 in accordance with a first embodiment of the present invention. Referring to FIG. 1, aroma display 50 includes a substantially columnar housing 60. Housing 60 includes a base housing 62, an aroma-cartridge-accommodating housing 64 and a cap 66 attached in this order on base housing 62. Cap 66 is detachable from aroma-cartridge-accommodating housing 64, and when an aroma cartridge is to be stowed in aroma display 50 or removed from aroma display 50, cap 66 is removed from aroma-cartridge-accommodating housing 64, as will be described later.

Cap 66 includes a cover having a bottom portion of a circular shape that fits an upper edge of aroma-cartridge-accommodating housing 64 and an upper surface gradually tapered upward to the center. The bottom portion of this cover is fixed on the upper edge (end portion of cap 66) of aroma-cartridge-accommodating housing 64. At the center of the cover of cap 66, an opening area 68 is formed, where openings as air outlets are collectively formed to emit scented air from aroma cartridges. At the opening area 68, an opening 70, of which diameter is about ¼ that of cap 66, is formed.

Figure 2:
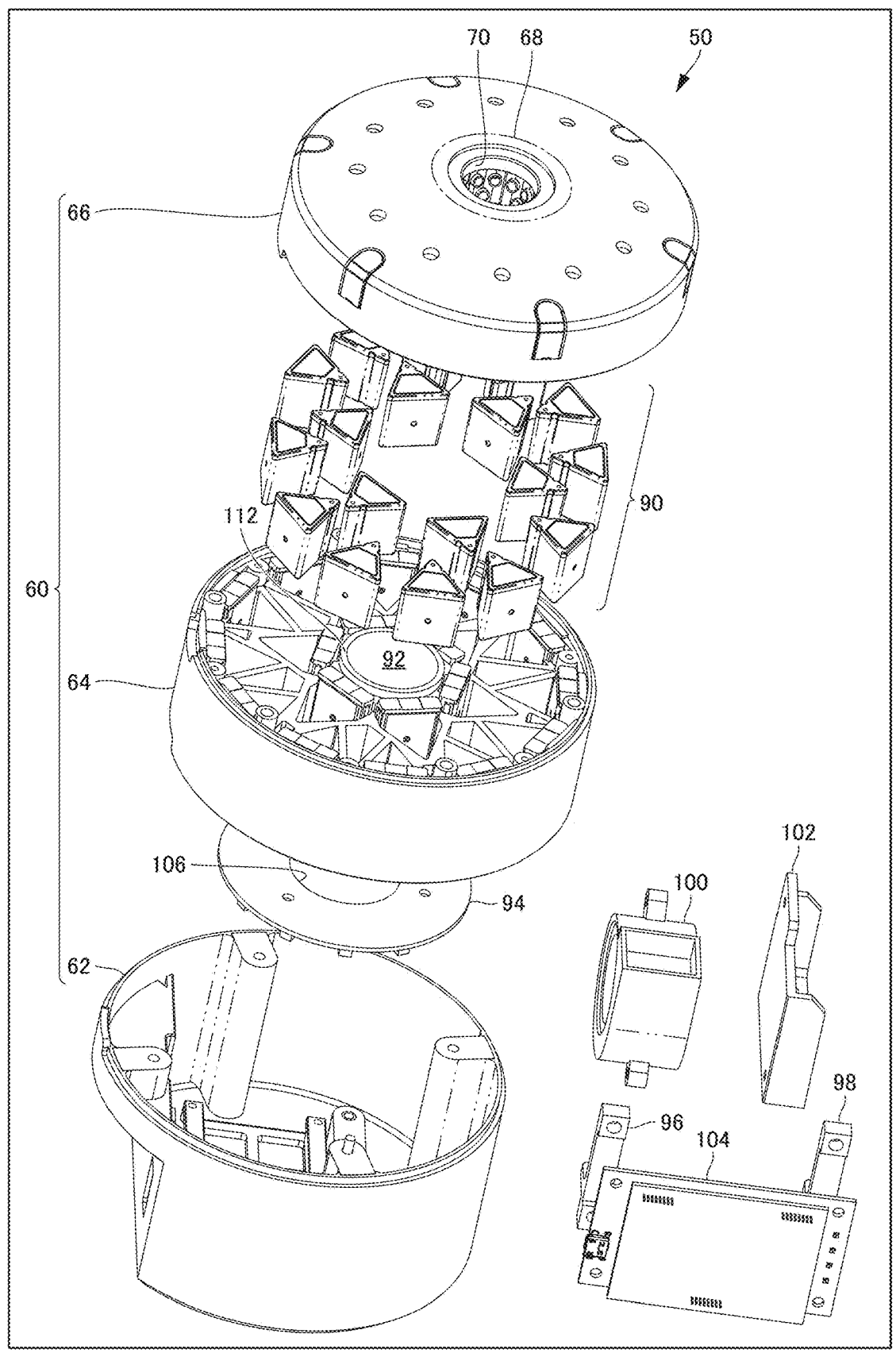
FIG. 2 is an exploded perspective view from obliquely above the aroma display shown in FIG. 1.
Figure 3:
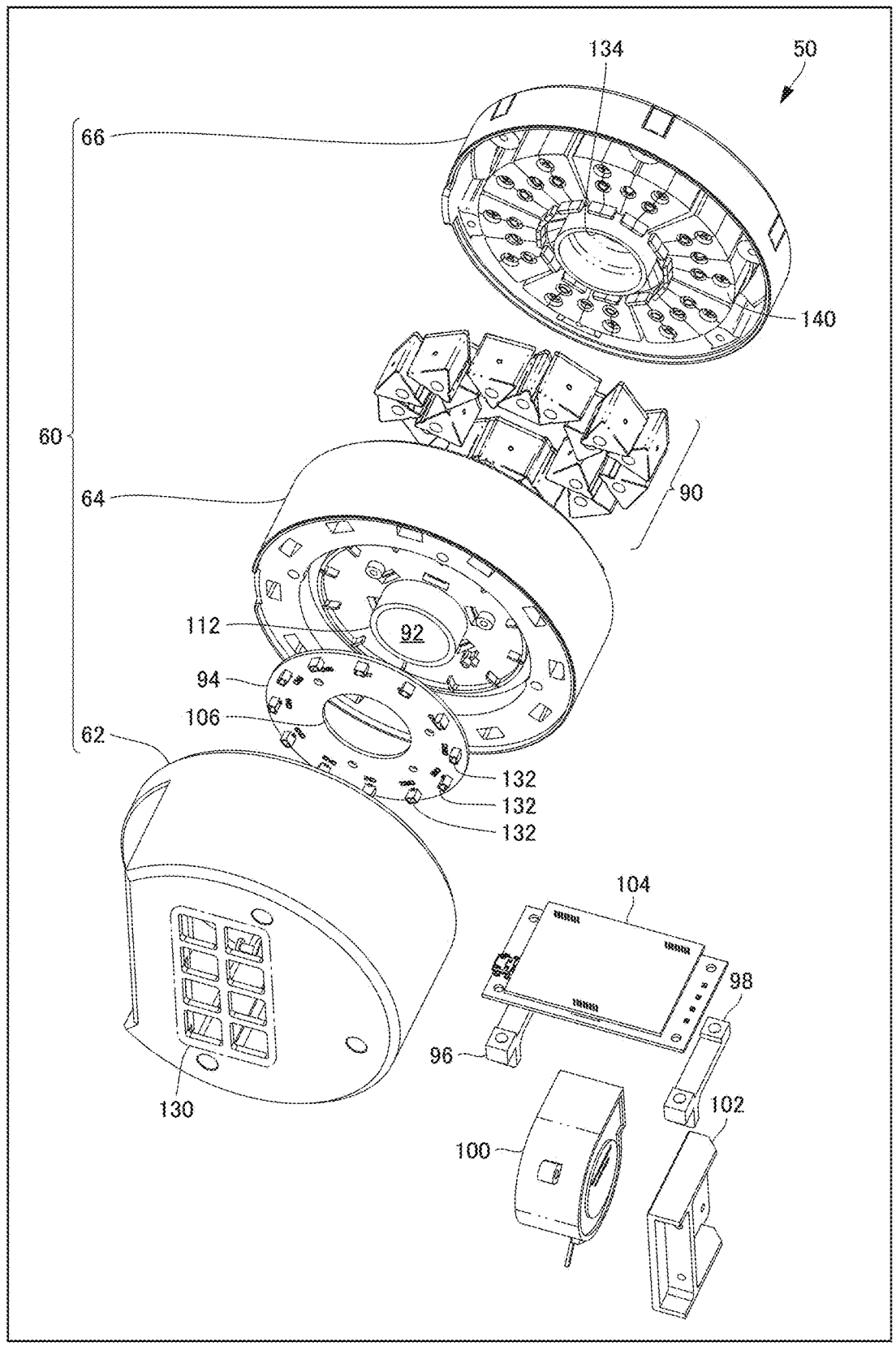
FIG. 3 is an exploded perspective view from obliquely below the aroma display shown in FIG. 1.

Referring to FIGS. 2 and 3, in the present embodiment, base housing 62 and aroma-cartridge-accommodating housing 64 have circular cross-sections. In aroma-cartridge-accommodating housing 64, a cartridge-loading section is formed, allowing loading of a plurality of aroma cartridges. As can be particularly seen from FIGS. 2 and 3, at the center of aroma-cartridge-accommodating housing 64, a duct member 112 defining an air passage 92 is provided, and around the duct member 112, a set 90 of the aroma cartridges including 18 aroma cartridges is stowed. Details of aroma cartridge set 90 will be described later. In the present embodiment, the set 90 of aroma cartridges is divided into an outer aroma cartridge group and an inner aroma cartridge group. Each of these groups of aroma cartridges is arranged on a circumference about the central axis of aroma-cartridge-accommodating housing 64. Details of the arrangement will be described later. The number of aroma cartridges may be selected as desired. As a prior art, an example including six aroma cartridges is disclosed and, therefore, in the aroma display of the present invention, it is preferred that at least six aroma cartridges are used for the outer group and at least one is used for the inner group. In the present embodiment, 12 aroma cartridges are loadable as the outer group and six are loadable as the inner group.

With reference to FIG. 3, at the center of the rear surface of cap 66 (the surface facing aroma-cartridge-accommodating housing 64), a lower edge of nozzle 134 forming opening 70 shown in FIG. 1 is placed. Around nozzle 134, six tube fixings including tube fixing 140 are arranged. Tube fixing 140 and the like fix a plurality of tubes on cap 66, the tubes respectively guiding scented air emitted from the set 90 of aroma cartridges to the vicinity of opening 70 inside nozzle 134. Structure of tube fixing 140 will be described later. The lower edge of nozzle 134 is in contact with an upper edge of duct member 112, the lower half of nozzle 134 has a conical shape having its radius gradually decreasing upward, and the upper half is a cylinder having both upper and lower ends opened, having an inner diameter smaller than the inner diameter of the lower edge. Because of such a shape of nozzle 134, the air flowing into the lower edge of nozzle 134 is accelerated in nozzle 134 and emitted from the opening at the upper edge.

Particularly referring to FIG. 3, on a lower surface of base housing 62, a plurality of openings 130 are formed to serve as air inlets, as will be described later. On the base housing 62, aroma-cartridge-accommodating housing 64 is attached. In base housing 62, a sirocco fan 100 as an air-emitting mechanism for emitting a scent-free air is attached by means of a fitting member 102. Sirocco fan 100 generates a scent-free air flow and feeds the flow to nozzle 134 provided on cap 66. In base housing 62, a control circuit board 104, which is capable of communication with the outside by wireless communication, is further attached by means of fitting members 96 and 98. Control circuit board 104 has mounted thereon a control circuit for controlling the sirocco fan 100 and a plurality of air-feeding mechanisms for emitting scented air by feeding air to the inside of each of the aroma cartridges of the set 90 of the aroma cartridges. The air-feeding mechanism for each cartridge is provided inside the aroma-cartridge-accommodating housing 64, as will be described later. In base housing 62, a battery, not shown, as a power source for control circuit board 104 is further contained.

In aroma-cartridge-accommodating housing 64, duct member 112 is fixed. As described above, duct member 112 defines an air passage 92 from sirocco fan 100 to opening 70. In the present embodiment, the central axis of aroma-cartridge-accommodating housing 64 matches the central axis of duct member 112. At a lower portion of duct member 112, a relay board 94 having a central opening 106 is attached. On the lower surface of relay board 94, NFC chips 132 for reading identifiers of respective aroma cartridges or their scents through near-field communication with NFC tags (not shown) adhered to bottom surfaces of aroma cartridges are provided at positions corresponding to respective aroma cartridges. Lower end of duct member 112 is arranged near a discharge outlet of sirocco fan 100 through an opening 106.

Figure 4:
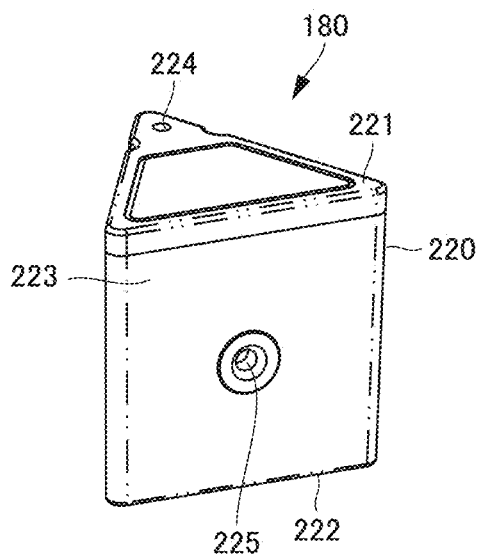
FIG. 4 is a perspective view from obliquely above an aroma cartridge.
Figure 5:
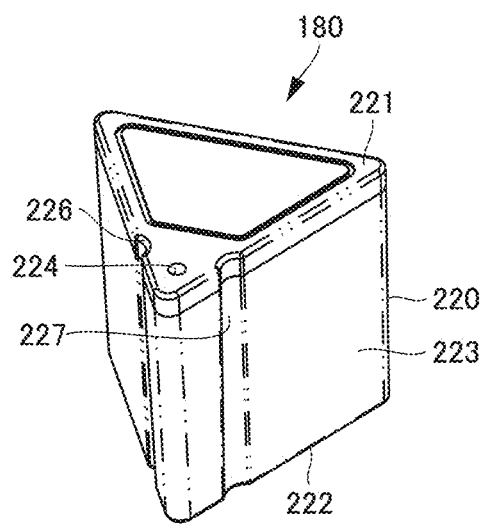
FIG. 5 is a perspective view of the aroma cartridge obliquely above in a direction opposite to FIG. 4.

Referring to FIGS. 4 and 5, by way of example, an aroma cartridge 180 has a triangular prism shape of which cross-section is substantially a regular triangle. Specifically, aroma cartridge 180 has a housing 220 consisting of upper and lower surfaces 221 and 222, which are regular triangles parallel to and congruent with each other, and a side surface 223 formed to connect their circumferences. Housing 220 has a hollow portion in which a scent source is sealed. In the vicinity of one vertex on upper surface 221 of aroma cartridge 180, a scent-emitting opening 224 is formed, connected to the hollow portion of housing 220, through which air including scent from the scent source sealed in housing 220 is emitted. In the present embodiment, assuming that the center of upper surface 221 is the geometric center of upper surface 221, scent-emitting opening 224 is off the center, at that position on a line connecting the center of upper surface 221 and the above-mentioned one vertex which divides the line about 4:1, on the side of the said one vertex. At that portion of the side surface 223 which is opposite to scent-emitting opening 224, an air-feeding inlet 225 is formed, allowing a micro-blower as an external air-feeding mechanism (which will be described later) to feed air to the hollow portion of housing 220. Further, as shown in FIG. 5, on side surfaces 223 on both sides of the vertex at which scent-emitting opening 224 is formed, grooves 226 and 227 are formed. These grooves 226 and 227 are used for positioning, when aroma cartridge 180 is loaded to cartridge-loading section of aroma-cartridge-accommodating housing 64.

Figure 6:
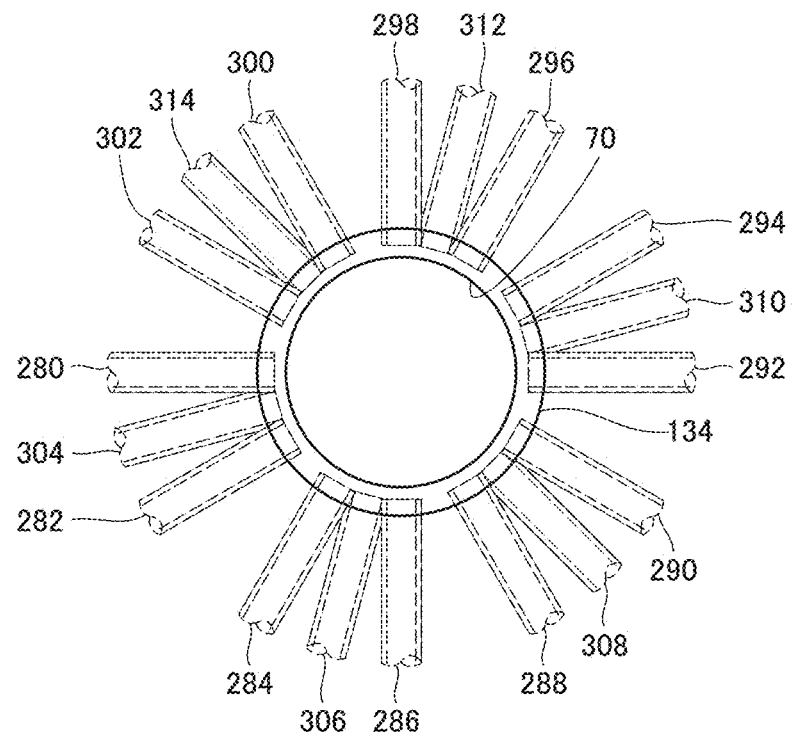
FIG. 6 is a plan view showing an arrangement of tubes around an opening area of a cap of the aroma display shown in FIG. 1.

FIG. 6 shows an arrangement of tubes near the opening 70 shown in FIG. 1. Referring to FIG. 6, around nozzle 134 forming opening 70, a first group of tubes 280, 282, . . . 300 and 302 for the first group of aroma cartridges, and a second group of tubes 304, 306, . . . 312 and 314 for the second group of aroma cartridges are concentrated, with end portions of the tubes opened to opening 70. As shown in FIG. 6, tubes 280, 282 and 304, tubes 284, 286 and 306, tubes 288, 290 and 308, tubes 292, 294 and 310, tubes 296, 298 and 312, and tubes 300, 302 and 314 form groups of three, respectively, Details of a mechanism that fixes each of these tubes on cap 66 will be described later.

Figure 7:
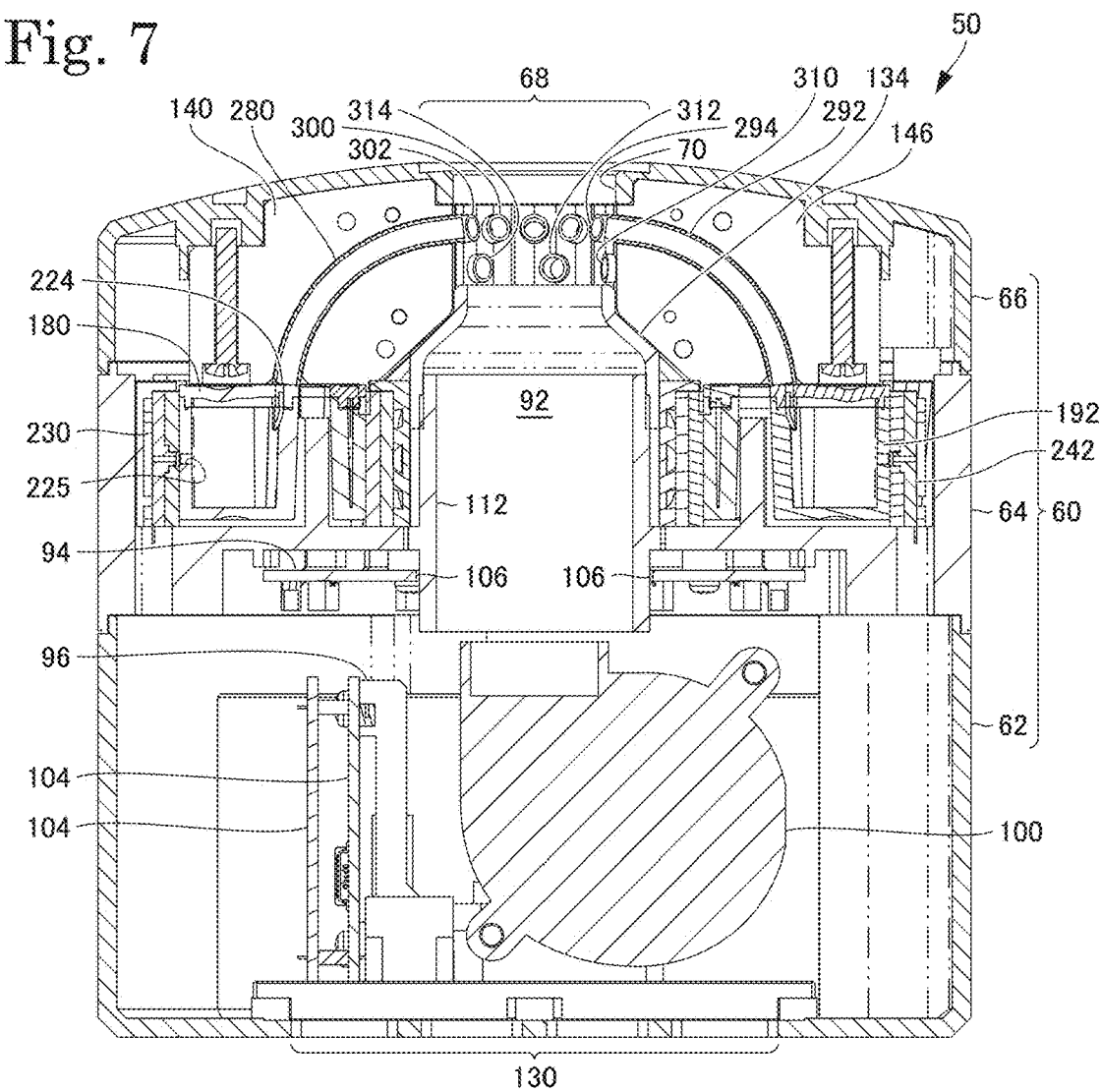
FIG. 7 is a cross-sectional view of the aroma display shown in FIG. 1, taken along the line 7-7.
Figure 8:
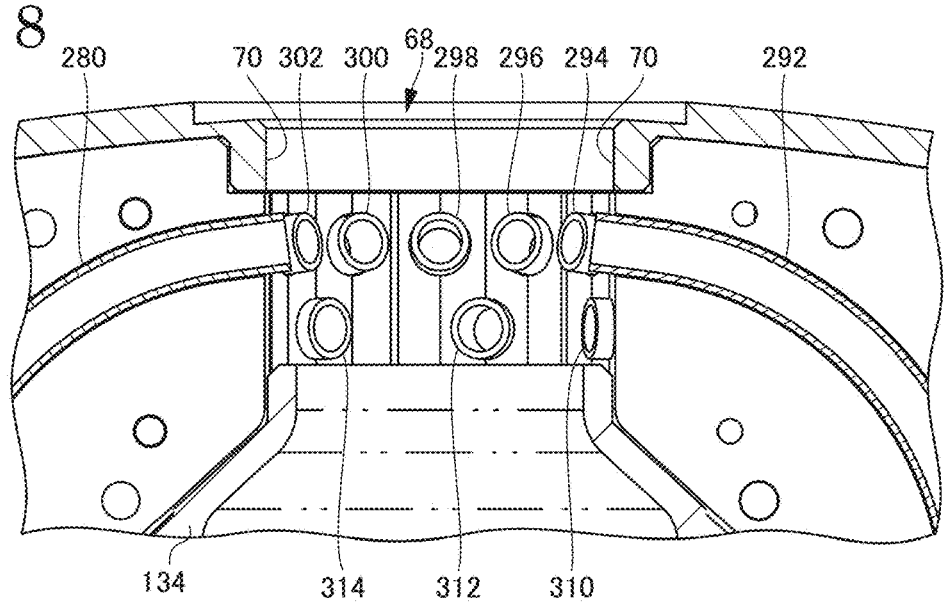
FIG. 8 shows in enlargement the opening area in the cross-sectional view of the aroma display of FIG. 7.

FIG. 7 is a cross-sectional view of aroma display 50 in the direction 7-7 of FIG. 1, and FIG. 8 is an enlarged view of a portion near opening area 68. Referring to FIG. 7, behind that portion of inner circumferential wall of aroma-cartridge-accommodating housing 64 where each of the outer aroma cartridges is loaded, a micro-blower is provided, which is operated by a piezoelectric element for generating an air flow. By way of example, behind aroma cartridge 180 belonging to the outer aroma cartridge group, a micro-blower 230 for feeding air to air-feeding inlet 225 of aroma cartridge 180 is provided. Similarly, for an aroma cartridge 192 loaded on the opposite side of aroma cartridge 180, a micro-blower 242 for feeding air to its air-feeding inlet is provided behind aroma cartridge 192. These micro-blowers are provided for each of the aroma cartridges of the outer group and inner group, and capable of supplying air individually to the air-feeding inlets of these aroma cartridges.

For example, to scent-emitting opening 224 of aroma cartridge 180, one end of tube 280 is attached in contact therewith for communicating scent-emitting opening 224 and opening 70. Tube 280 is attached to the surface of cap 66 by tube fixing 140. Tube fixing 140 fixes tube 280 to cap 66 such that the other end of tube 280 opens inside the opening 70 formed in cap 66. The same applies to aroma cartridge 192, and tube 292 is attached with its one end in contact with the scent-emitting opening. Tube 292 is also attached to cap 66 by means of a tube fixing 146 similar to tube fixing 140, such that the other end thereof opens toward the center of cap 66 from circumferential wall of cap 66. By such an arrangement, scented air emitted from aroma cartridges 180 and 192 is guided through tubes 280 and 292, respectively, to opening 70 and emitted to the center of opening 70. When air generated by sirocco fan 100 is being emitted from nozzle 134, the scented air is carried by the air flow emitted from nozzle 134. As a result, it becomes possible to transmit the scented air considerably far from aroma display 50. When sirocco fan 100 is stopped, the scented air remains near opening area 68. As a result, the scent is felt only in the vicinity of aroma display 50.

Tubes 294, 296, 298, 300, 302 and so on shown in FIGS. 7 and 8 are also for guiding the scented air emitted from openings of corresponding aroma cartridges of the outer aroma cartridge group to opening 70. Tubes 310, 312 and 314 shown in FIGS. 7 and 8 are for the aroma cartridges belonging to the inner aroma cartridge group, as will be described later.

Figure 9:
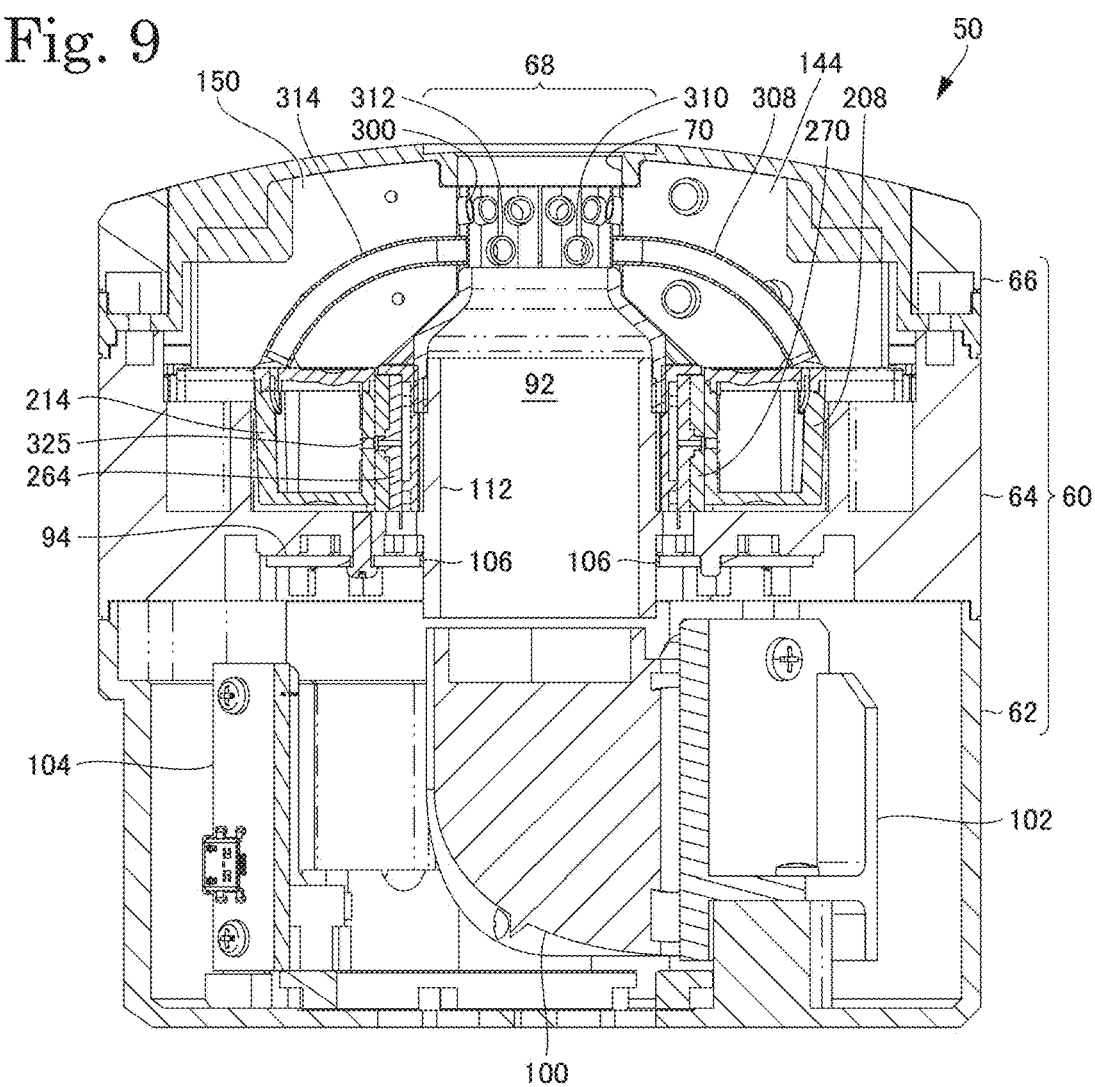
FIG. 9 is a cross-sectional view of the aroma display shown in FIG. 1, taken along the line 9-9.
Figure 10:
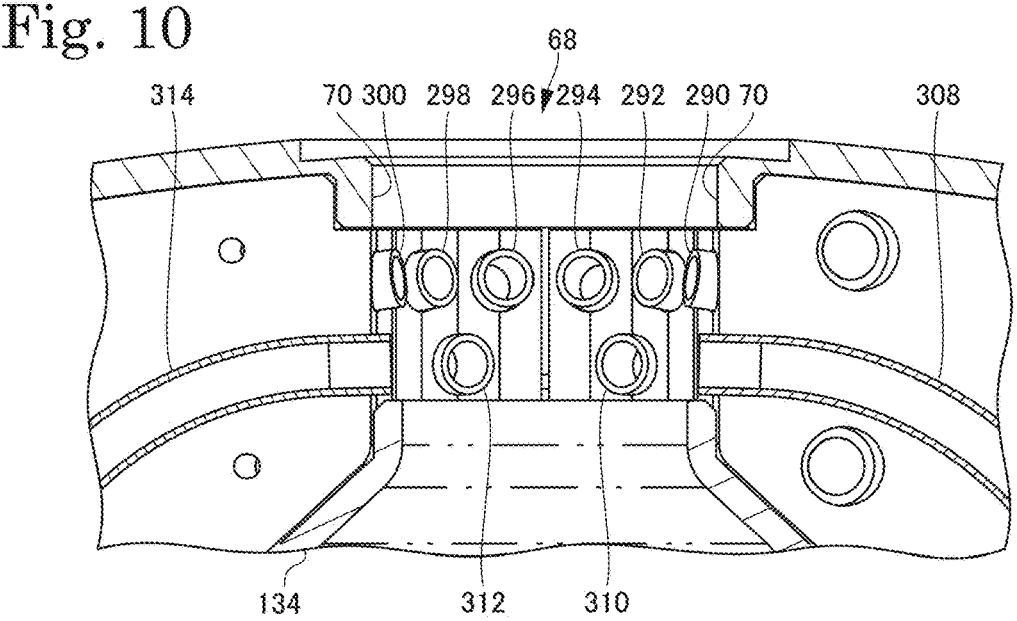
FIG. 10 shows in enlargement the opening area in the cross-sectional view of the aroma display of FIG. 9.

FIG. 9 is a cross-sectional view of aroma display 50 in the direction 9-9 of FIG. 1, and FIG. 10 is an enlarged view of a portion near opening area 68. Referring to FIG. 9, at that portion of an outer circumferential wall of duct member 112 inside aroma-cartridge-accommodating housing 64 where each of the aroma cartridges belonging to the inner cartridge group is loaded, a micro-blower for generating an air flow is provided. By way of example, an aroma cartridge 214 belonging to the inner aroma cartridge group is loaded to cap 66 facing opposite side to outer aroma cartridge group, such that the scent-emitting opening is positioned away from the central axis of aroma-cartridge-accommodating housing 64. Behind the cartridge (at that portion of the side surface at which air-feeding inlet 325 is formed), a micro-blower 264 is provided for introducing air to air-feeding inlet 325 of aroma cartridge 214. Similarly, for an aroma cartridge 208 loaded on the opposite side of aroma cartridge 214, a micro-blower 270 for feeding air to its air-feeding inlet is provided behind aroma cartridge 208 on the outer circumference of duct member 112.

By way of example, at the scent-emitting opening of aroma cartridge 214, tube 314 is attached with its one end in contact with the opening. Tube 314 is attached to a rear surface of the cover of cap 66 by means of a tube fixing 150. Tube fixing 150 fixes tube 314 on cap 66 such that the other end of tube 314 opens into opening 70 formed in cap 66. The same applies to aroma cartridge 208, and to its scent-emitting opening, tube 308 is attached with its one end in contact therewith. Tube 308 is also attached to cap 66 by a tube fixing 144 such that the other end opens into opening 70 formed in cap 66. By such an arrangement, scented air emitted from aroma cartridges 214 and 208 is guided through tubes 314 and 308, respectively, to opening 70 and emitted to the center of opening 70.

Tubes 312 and 310 shown in FIG. 10 are also for guiding scented air emitted from scent-emitting openings of corresponding aroma cartridges of the inner aroma cartridge group to the opening 70. Tubes 290, 292, 294, 296, 298 and 300 shown in FIG. 10 are tubes for the aroma cartridges belonging to the outer aroma cartridge group.

As shown in FIGS. 8 and 10, in the present embodiment, end portions on the side of opening 70 of tubes for the outer aroma cartridge group are arranged on a circumference in opening 70 about the central axis of a plane that is perpendicular to the central axis of opening 70. Similarly, end portions on the side of nozzle 134 of tubes for the inner aroma cartridge group are arranged, similar to the outer aroma cartridge group, on a circumference in opening 70 about the central axis of a plane that is perpendicular to the central axis. It is noted, however, that the circle is on a plane different from the plane of the circle on which tube ends for the outer aroma cartridge group are positioned. By arranging end portions of aroma cartridges on different planes, it becomes possible to arrange all tubes inside the opening 70 even when the number of aroma cartridges increases and it becomes difficult to ensure sufficient space for forming openings therefor inside the opening 70. Therefore, even when the number of aroma cartridges to be loaded to aroma display 50 increases, it is possible to ensure the space for tube openings to some extent, without increasing the inner diameter of opening 70.

Figure 11:
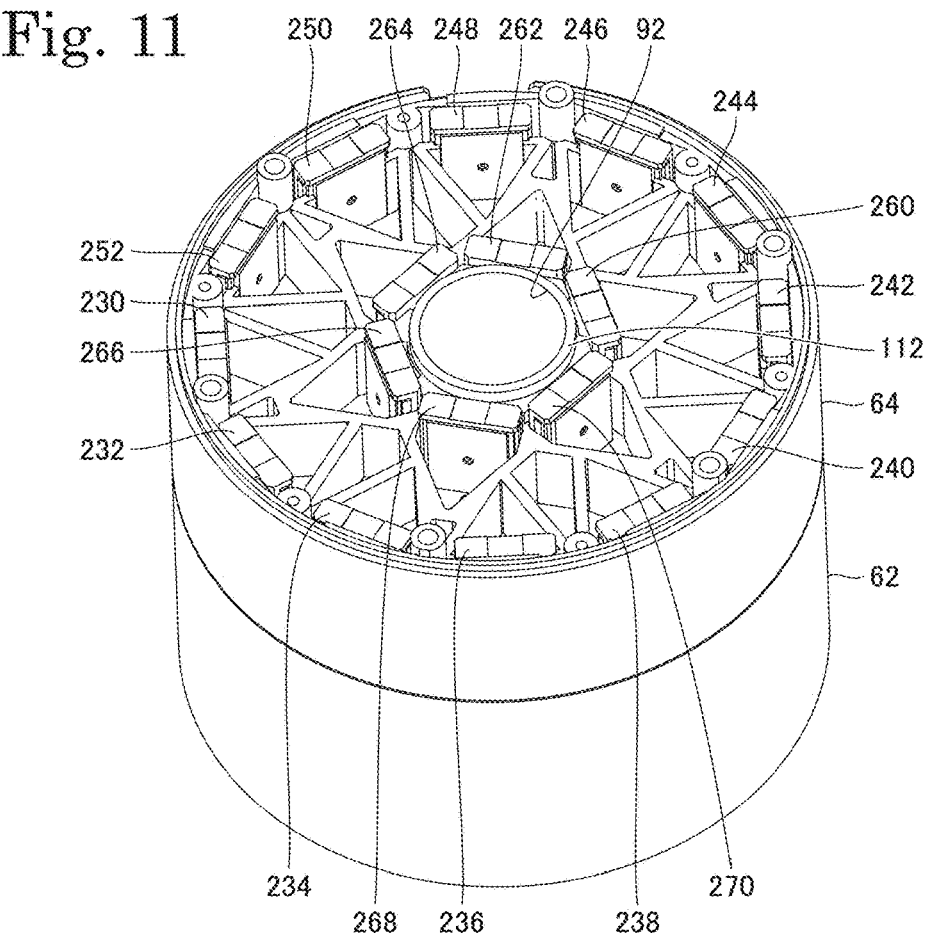
FIG. 11 is a perspective view of a housing of the aroma display shown in FIG. 1, with its cap removed.
Figure 12:
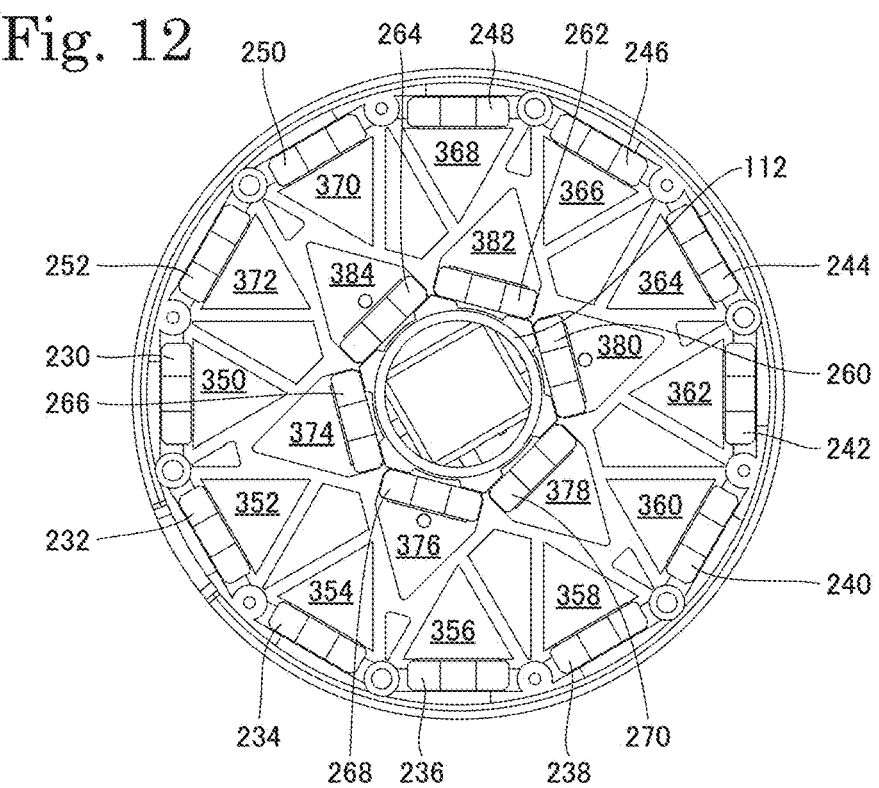
FIG. 12 is a plan view of the housing of the aroma display with its cap removed, shown in FIG. 11.
Figure 13:
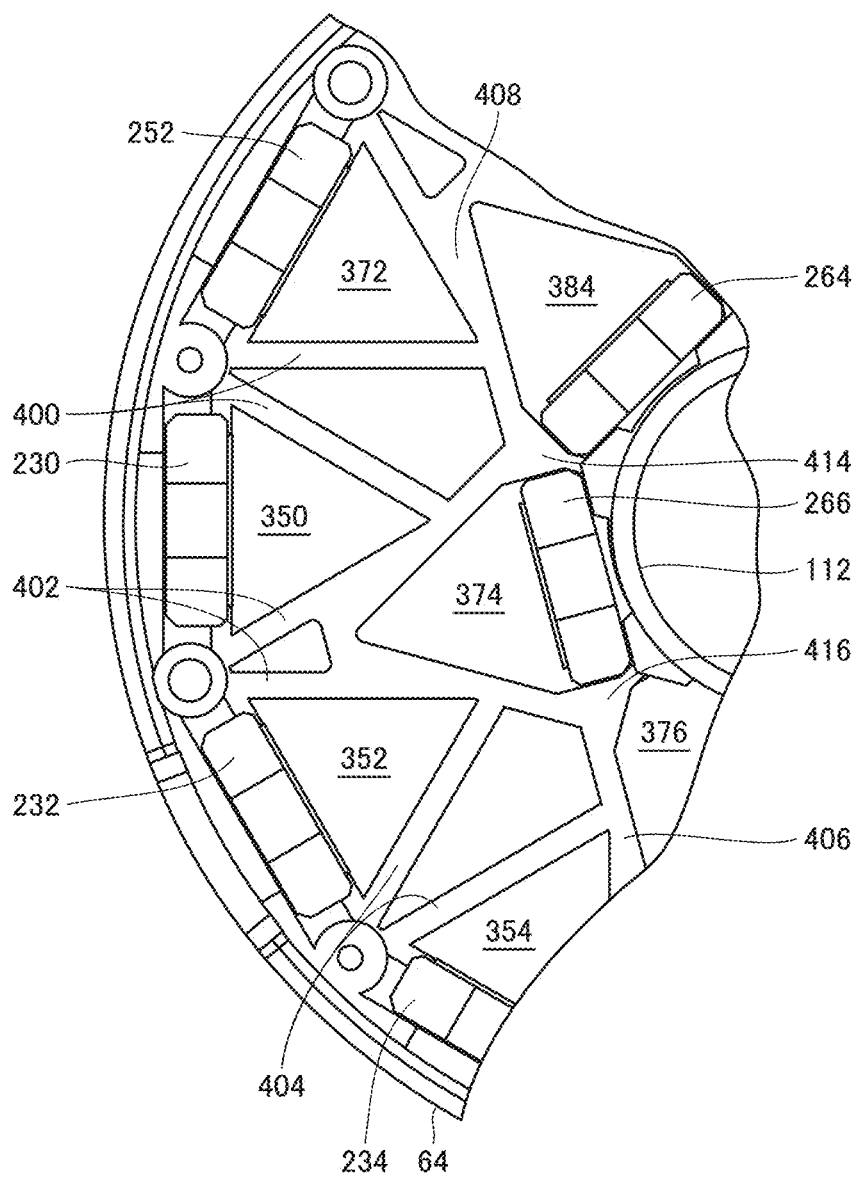
FIG. 13 is a plan view showing in enlargement a portion of FIG. 12.
Figure 14:
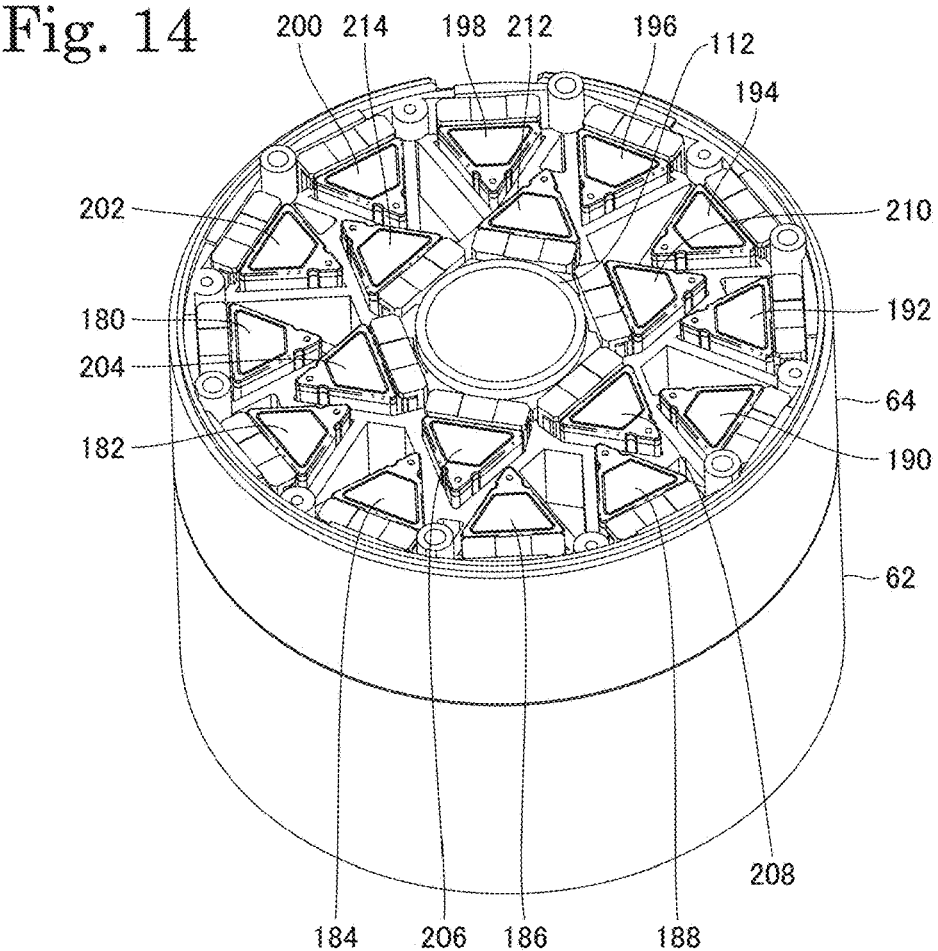
FIG. 14 is a perspective view of the housing of the aroma display with its cap removed, when the aroma cartridge is loaded.
Figure 15:
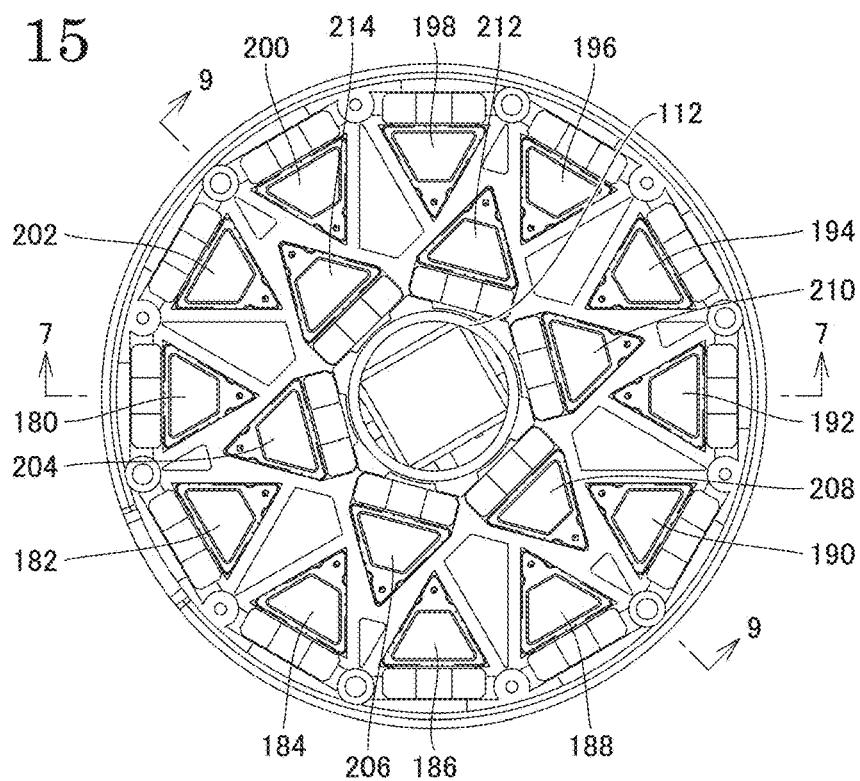
FIG. 15 is a plan view of the housing of the aroma display shown in FIG. 14.
Figure 16:
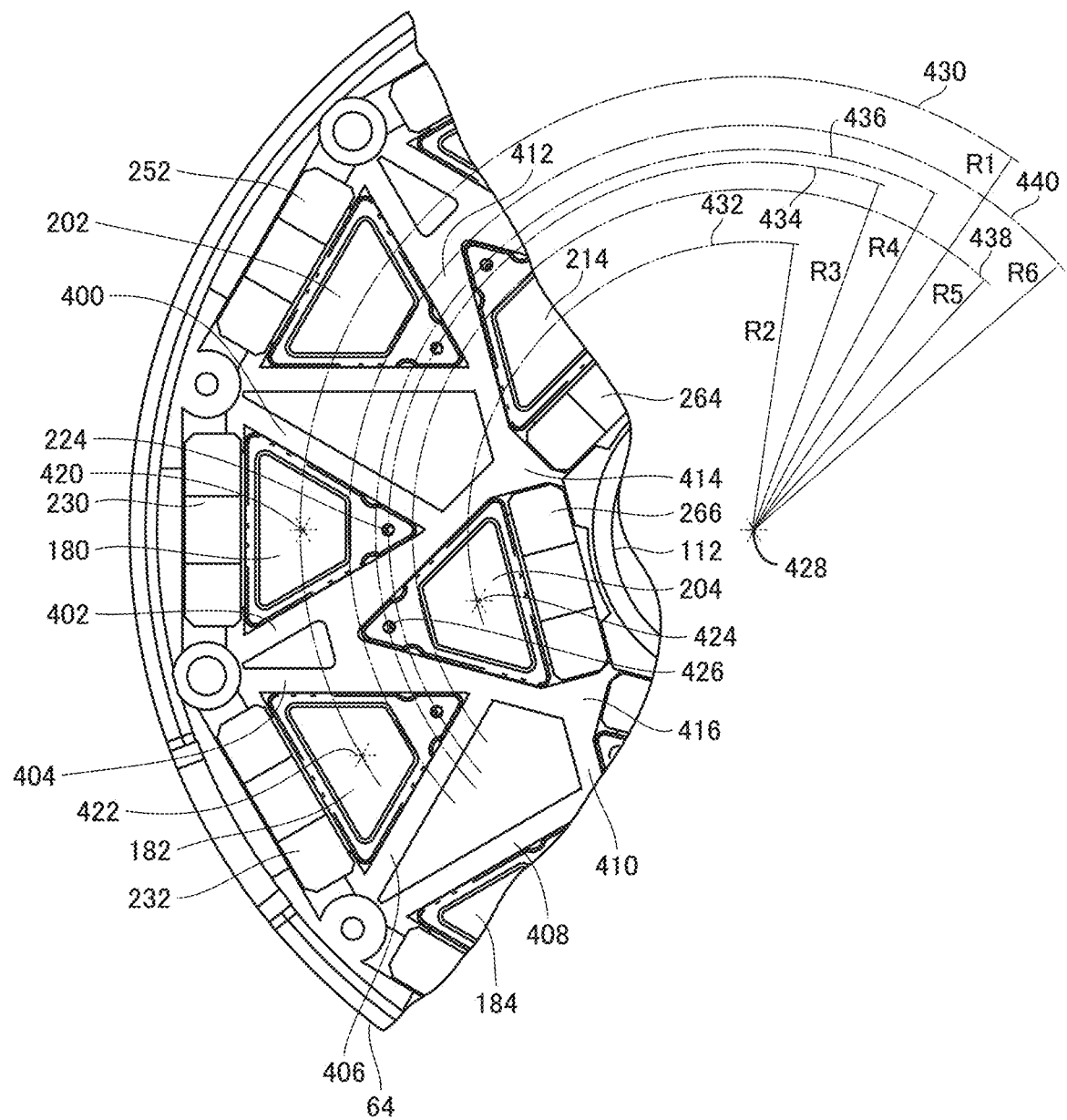
FIG. 16 is a plan view showing in enlargement a portion of FIG. 15.

FIGS. 11 and 12 are perspective view and plan view, respectively, of aroma-cartridge-accommodating housing 64 with cap 66 removed from aroma-cartridge-accommodating housing 64. In these figures, housing 60 is loaded with no aroma cartridge. FIG. 13 shows, in enlargement, a portion of FIG. 12. FIGS. 14 and 15 are perspective view and plan view of aroma-cartridge-accommodating housing 64 loaded with twelve aroma cartridges 180, 182, . . . , 200 and 202 of the outer group as well as six aroma cartridges 204, 206, . . . 212 and 214 of the inner group. FIG. 16 shows, in enlargement, a portion of FIG. 15.

Referring to FIGS. 11, 12 and 13, in the present embodiment, a cartridge-loading section consisting of outer cartridge-loading chambers 350, 352, . . . 370 and 372 and inner cartridge-loading chambers 374, 376, . . . , 382 and 384 is formed in aroma-cartridge-accommodating housing 64. Each cartridge-loading chamber is for containing one aroma cartridge. Among these cartridge-loading chambers, cartridge-loading chambers 350, 352, . . . 370 and 372 are arranged at positions of rotation symmetry about the central axis of cap 66, forming an outer cartridge-loading section. Each of these cartridge-loading chambers forms a space of regular triangle, and one vertex of each such space faces the central axis of the cap 66. On the other hand, cartridge-loading chambers 374, 376, . . . , 382 and 384 each define a regular triangular hollow space in the similar manner. However, these are arranged with one vertex positioned in rotation symmetry about the central axis to face the direction opposite to the central axis of cap 66, forming the inner cartridge-loading section. Assuming that the center of each of these regular triangles is the geometric center, the distance from each of the outer cartridge-loading chambers 350, 352, . . . , 370 and 372 to the central axis is identical. Here, the distance from the geometric center of regular triangle of each cartridge-loading chamber to the central axis will be referred to as the distance between the cartridge-loading chamber and the central axis. Further, the distance from each of the inner cartridge-loading chambers 374, 376, . . . , 382 and 384 to the central axis is identical. The distance from the outer cartridge-loading chamber to the central axis is longer than the distance from the inner cartridge-loading chamber to the central axis.

Referring to FIG. 13, by way of example, between cartridge-loading chambers 350 and 352, cartridge-loading chamber 374 is formed. Further, while cartridge-loading chamber 372 is formed next to cartridge-loading chamber 350, there is no inner cartridge-loading chamber formed between these. Regarding this difference, in aroma-cartridge-accommodating housing 64, a total of six V-shaped partition members 400, 404, . . . are provided to separate the outer cartridge-loading chambers between which no inner cartridge-loading chamber is formed. The open side of this V-shaped partition members 400, 404, . . . is fixed on an outer circumference of duct member 112 by means of fixing members 414, 416 and so on. Between cartridge-loading chambers where a cartridge-loading chamber is formed as in the case of, for example, cartridge-loading chambers 350 and 352 between which cartridge-loading chamber 374 is formed, six inverted A-shaped partition members 402, 406, 408 . . . are formed. Each of the legs of this inverted A merges with the upper end of adjacent partition member 400 etc. to be fixed on the outer circumference of duct member 112 by means of fixing member 414, 416 or the like. As shown in FIG. 13, on the inner circumference of outer wall of aroma-cartridge-accommodating housing 64, twelve micro-blowers 230, 232, . . . 250 and 252 are fixed at positions fitting air-feeding inlets of aroma cartridges loaded to cartridge-loading chambers 350, 352, . . . 370 and 372. Further, on the outer circumference of the outer wall of duct member 112, six micro-blowers 260, 262, . . . 268 and 270 are fixed at positions fitting air-feeding inlets of aroma cartridges loaded to cartridge-loading chambers 374, 376, . . . 382 and 384.

Micro-blowers 230, 232, . . . , 250 and 252 as well as micro-blowers 260, 262, . . . 268 and 270 generate wind by receiving AC voltage. The AC voltage for this purpose is generated and output by a control circuit mounted on control circuit board 104 (see FIGS. 2 and 3). This control circuit drives micro-blowers 230, 232, . . . , 250 and 252 as well as micro-blowers 260, 262, . . . 268 and 270 and sirocco fan 100 appropriately in accordance with information externally applied through wireless communication.

As shown in FIGS. 13, 14 and 15, to outer cartridge-loading chambers 350, 352, . . . , 370 and 372 (see FIG. 13), aroma cartridges 180, 182, . . . , 200 and 202 (see FIGS. 14 and 15) are loaded, respectively. To inner cartridge-loading chambers 374, 376, . . . , 382 and 384 (see FIG. 13), aroma cartridges 204, 206, . . . , 212 and 214 (see FIGS. 14 and 15) are loaded, respectively. The cross section taken along the line 7-7 of FIG. 15 is that shown in FIG. 7, and the cross section taken along the line 9-9 of FIG. 15 is that shown in FIG. 9 (it is noted that in both FIGS. 7 and 9, cap 66 is not shown). Of these aroma cartridges, aroma cartridges 180, 182, . . . , 200 and 202 belonging to the outer group are loaded in aroma-cartridge-accommodating housing 64 such that their upper surfaces are flush on one same plane. Aroma cartridges 204, 206, . . . , 212 and 214 belonging to the inner group are also loaded in aroma-cartridge-accommodating housing 64 such that their upper surfaces are flush on one same plane. Though the plane on which upper surfaces of aroma cartridges belonging to the outer group are positioned is the same plane on which upper surfaces of aroma cartridges belonging to the inner group are positioned in the present embodiment, the planes may be different from each other.

FIG. 16 shows the two-dimensional positional relation between the aroma cartridges of the outer group and the aroma cartridges of the inner group. Referring to FIG. 16, the centers of aroma cartridges of the outer group (for example, the center 420 of aroma cartridge 180, the center 422 of aroma cartridge 182, and so on) are all on the first circle 430 of which center is the central axis 428 of aroma-cartridge-accommodating housing 64. Assume that the first circle 430 has a radius R1. Similarly, the centers of aroma cartridges of the inner group (for example, the center 424 of aroma cartridge 204) are on the second circle 432 of which center is the central axis 428. Assume that the second circle 432 has a radius R2. As can be clearly seen, R1>R2.

Further, scent-emitting opening of the aroma cartridge belonging to the outer group (for example, scent-emitting opening 224 of aroma cartridge 180) is on the third circle 434 of radius R3 of which center is the central axis 428. Similarly, scent-emitting opening of the aroma cartridge belonging to the inner group (for example, scent-emitting opening 426 of aroma cartridge 204) is on the fourth circle 436 of radius R4 of which center is the central axis 428.

Further, the vertexes closest to the scent-emitting openings of outer group aroma cartridges are on the fifth circle 438 of radius R5 of which center is the central axis 428. Similarly, the vertexes closest to the scent-emitting openings of inner group aroma cartridges are on the sixth circle 440 of radius R6 of which center is the central axis 428.

If R5=R6, it means that the vertexes of respective cartridges that are closest to the scent-emitting openings exist on one same circle. It is possible to accommodate eighteen aroma cartridges in aroma-cartridge-accommodating housing 64. However, the distance from the outer circumference of duct member 112 to the inner circumference of aroma-cartridge-accommodating housing 64 is substantially equal to the sum of the height of two cartridges and the height of two micro-blowers. If R5>R6, this distance further increases, which is not preferable from the viewpoint of making compact the aroma-cartridge-accommodating housing 64. Therefore, it is preferred that R5≤R6. On the other hand, it is desirable that the distance from each aroma cartridge to opening 70 is the same, and the difference in this distance is undesirable since timing of emitting scented air differs accordingly. Therefore, preferably, R3≈R4 (R3 is nearly equal to R4). The absolute value of difference between R3 and R4 should be up to about 10% and more preferably, up to about 5%, of the height of regular triangle of the plane of aroma cartridge. If the object is to further reduce the size of aroma-cartridge-accommodating housing 64, it is desirable to have R4>R3. The relation between R3 and R4 in this case will be described later with reference to the second embodiment.

Figure 17:
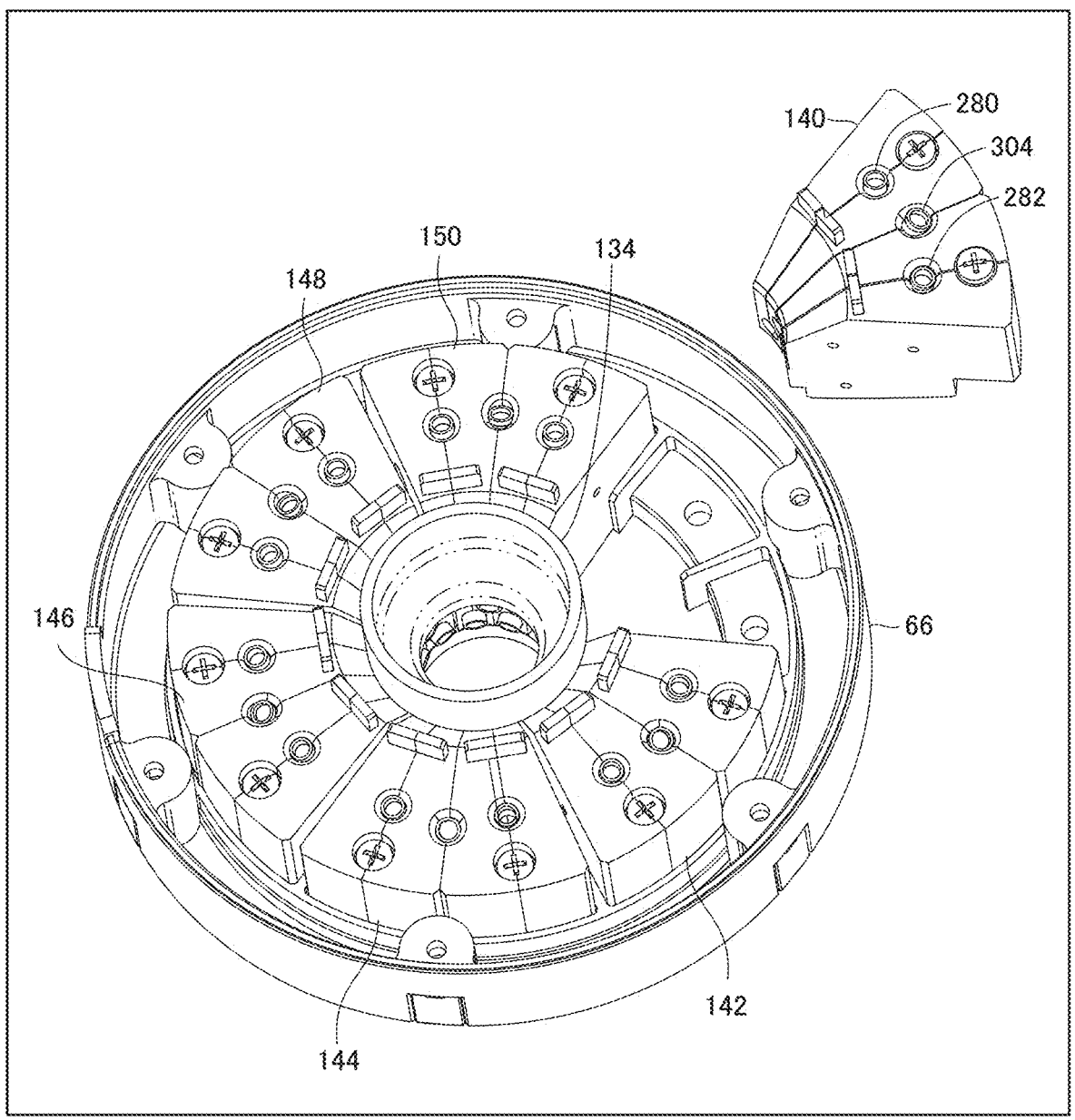
FIG. 17 is a perspective view of a rear surface of the cap and tube fixings.

FIG. 17 is a perspective view of the rear surface of cap 66. Referring to FIG. 17, on the rear surface of the cover of cap 66, six tube fixings 140, 142, . . . , 148 and 150 are fixed at six positions, respectively. FIG. 17 shows only one tube fixing 140 removed from cap 66. These tube fixings 140, 142, . . . , 148 and 150 are for fixing on cap 66 tubes for respective sets of any of the six inner aroma cartridges and neighboring two outer aroma cartridges. In the example shown in FIG. 17, tube fixing 140 is for fixing tubes 304, 280 and 282 (see FIG. 6) of aroma cartridge 204 shown in FIG. 15 at the center and aroma cartridges 180 and 182 on both sides thereof to cap 66. As shown in FIG. 17, tube fixings 140, 142, . . . , 148 and 150 are arranged at six rotation symmetry positions about the center of cap 66, that is, about the center of nozzle 134 (FIG. 6).

Figure 18:
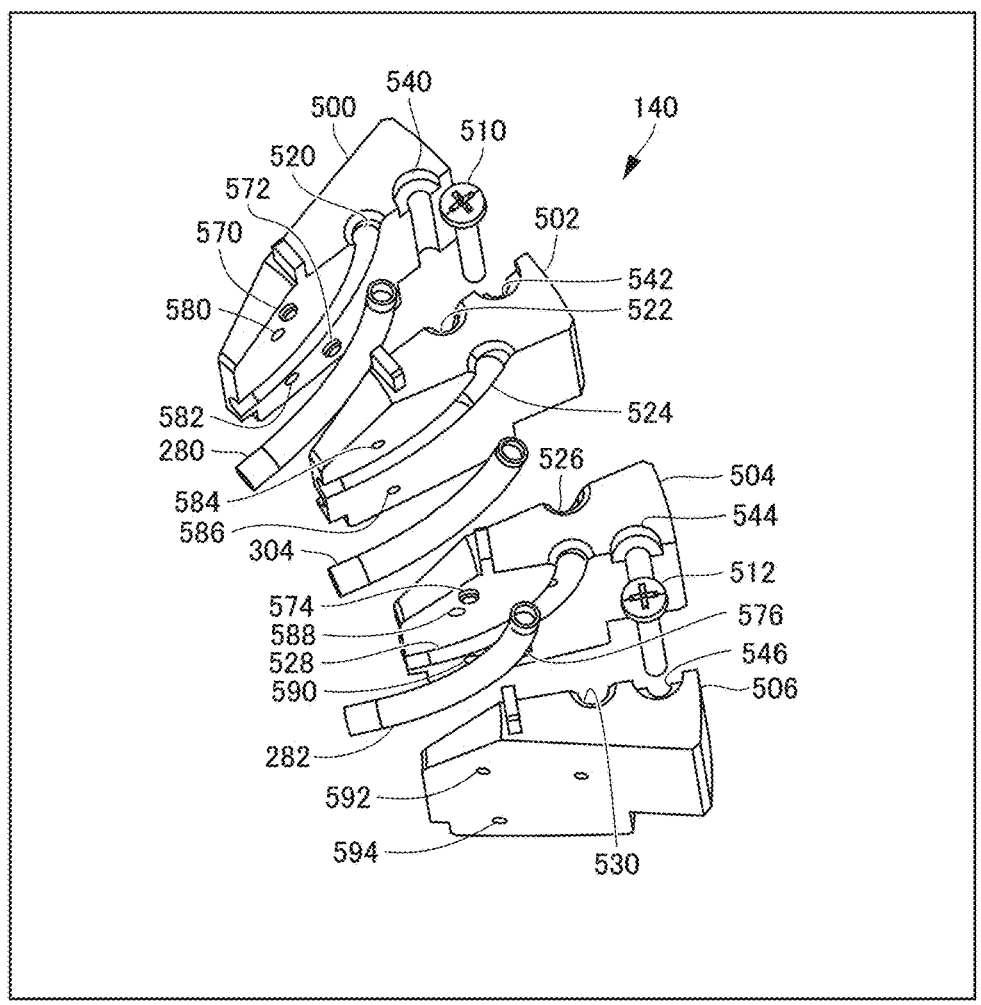
FIG. 18 is an exploded perspective view of the tube fixing.
Figure 19:
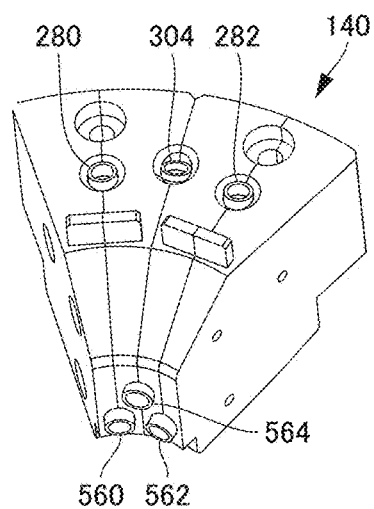
FIG. 19 is a perspective view of the tube fixing.
Figure 20:
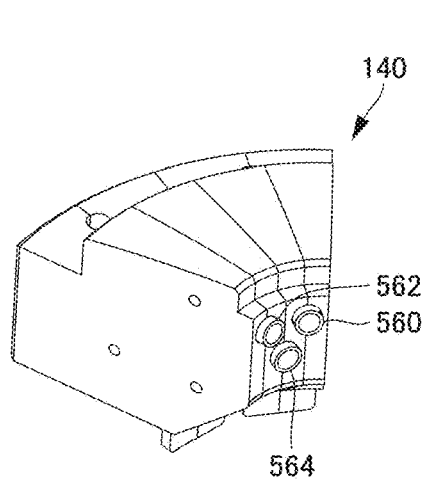
FIG. 20 is a perspective view of the rear side of tube fixing.

Referring to FIGS. 18 to 20, by way of example, tube fixing 140 has a first member 500 having a groove 520 and a screw hole 540, and a second member 502 having a groove 522 and a screw hole 542 formed on the surface facing the first member 500 and a groove 524 formed on the opposite surface. On a surface of first member 500 facing the second member 502, two small protrusions 570 and 572 are formed, and on the surface of second member 502 facing the first member 500, two small recesses, not shown, are formed at the corresponding positions. Between two side surfaces of first member 500, screw holes 580 and 582 are formed, and at corresponding positions of two side surfaces of second member 502, screw holes 584 and 586 are formed. The first and second members 500 and 502 are combined such that tube 280 is gripped between grooves 520 and 522. In this example, by fitting protrusions 570 and 572 formed on the first member 500 to the recesses formed on the surface of the second member 502, the first and second members 500 and 502 are coupled. By coupling the first and second members 500 and 502 in this manner, a screw hole to which a screw 510 is inserted, is formed by screw holes 540 and 542.

Tube fixing 140 further includes a third member 504 having a groove 526 formed on a surface facing the second member 502 and a groove 528 and a screw hole 544 formed on the opposite surface, and a fourth member 506 having a groove 530 and a screw hole 546 on a surface facing the third member 504. On the surface of third member 504 facing the fourth member 506, small protrusions 574 and 576 are formed, and on the surface of the fourth member 506 facing the third member 504, a small recess, not shown, is formed. Further, between two side surfaces of the third and fourth members 504 and 506, small screw holes 588 and 590 and screw holes 592 and 594 are formed, respectively. The third and fourth members 504 and 506 are combined such that tube 282 is gripped therebetween. At this time, the third and fourth members 504 and 506 are coupled by fitting the protrusions 574 and 576 formed on the third member 504 to the recess formed on the fourth member 506. By coupling the third and fourth members 504 and 506 in this manner, a screw hole to which a screw 512 is inserted, is formed by screw holes 544 and 546.

Finally, the coupled body of first and second members 500 and 502 is combined with the coupled body of third and fourth members 504 and 506 such that tube 304 is gripped between the groove 524 on the second member 502 and the groove 526 on the third member 504 and connected by means of putting screws to screw holes 580, 582, . . . , 592 and 594. Thus, tube fixing 140 is prepared.

By inserting screws 510 and 512 to the screw holes formed in tube fixing 140 and screwing screws 510 and 512 in screw holes formed on the rear surface of cap 66, tube fixing 140 is fixed on the rear surface of the cover of cap 66.

Referring to FIGS. 19 and 20, grooves 520 and 522 are formed at positions determined in advance such that when tube fixing 140 is fixed on cap 66, one end of tube 280 comes into contact with the scent-emitting opening 224 (see FIG. 4) of corresponding aroma cartridge 180 and that the other end 560 is opened to the inside of opening 70. Similarly, grooves 524 and 526 are formed at positions determined in advance such that one end of tube 304 comes into contact with the scent-emitting opening of corresponding aroma cartridge and that the other end 564 is opened to the inside of opening 70. Similarly, grooves 528 and 530 are formed at positions determined in advance such that one end of tube 282 comes into contact with the scent-emitting opening of corresponding aroma cartridge and that the other end 562 is opened to the inside of opening 70. As shown in FIGS. 19 and 20, ends 560 and 562 are positioned to be at the same height when tube fixing 140 is fixed on cap 66. End 564 is positioned beforehand to be slightly lower than the positions of ends 560 and 562.

Other tube fixings 142, 144, . . . , 148 and 150 also have the same structures and, therefore, detailed description thereof will not be repeated.

By way of example, tube 280 may be formed of a common resin such as polyethylene, polypropylene, polyethylene terephthalate, acryl, polyvinyl chloride and polycarbonate. In the present embodiment, inner wall of tube 280 and so on is coated with a fluororesin (polytetrafluoroethylene, ethylene-tetrafluoroethylene copolymer, perfluoroalkoxyalkane, perfluoroethylene-propene copolymer, polyvinylidene fluoride, polychlorotrifluoroethylene, ethylenechlorotrifluoroethylene copolymer etc.). As is well known, fluororesin is slippery and non-sticking. When scented air is emitted to the outside through such a tube, scent material hardly sticks on the inside of the tube. Therefore, it is possible to prevent undesirable blending of a scent from an aroma cartridge with another scent adhered and lingering in aroma display 50, when aroma cartridges are switched.

The above-described effect can also be attained by forming the tube using a common resin mixed with fluororesin, rather than coating the inner wall of a resin tube with fluororesin.

<Operation>

Aroma display 50 described above operates in the following manner. For using aroma display 50, first, necessary aroma cartridges, such as cartridge 180 and so on, are loaded to the inside of aroma-cartridge-accommodating housing 64. In the present embodiment, it is possible to load twelve aroma cartridges 180, 182, . . . , 200 and 202 as outer group aroma cartridges and six aroma cartridges 204, 206, . . . , 212 and 214 as inner group aroma cartridges to aroma-cartridge-accommodating housing 64. Specifically, at most eighteen aroma cartridges can be loaded to aroma display 50. When an aroma cartridge is loaded to aroma display 50, an NFC chip 132 in aroma display 50 reads an identifier of the aroma cartridge or its scent through near field communication from an NFC tag, not shown, attached to the aroma cartridge. The identifier is transmitted through control circuit board 104 to an external control device (for example, a computer). Based on this information and a scenario prepared in advance, the external control device generates a control signal related to which scent is to be emitted from which aroma cartridge at which timing or when sirocco fan 100 is to be operated, and transmits the signal to control circuit board 104. At a timing designated by the control signal, control circuit board 104 transmits driving signals to micro-blowers 230, 232, . . . , 250 and 252 and micro-blowers 260, 262, . . . , 268 and 270 corresponding to the designated aroma cartridge or cartridges as well as to sirocco fan 100. Receiving the driving signal, micro-blowers 230, 232, . . . , 250 or 252 or micro-blowers 260, 262, . . . , 268 or 270 or sirocco fan 100 operates in accordance with the driving signal so that scented air is emitted from the aroma cartridge. At this time, it is possible to drive two or more micro-blowers simultaneously, or to drive only one micro-blower. Further, it is possible to drive sirocco fan 100 simultaneously with driving of micro-blowers 230, 232, . . . , 250 or 252 or micro-blowers 260, 262, . . . , 268 or 270, and it is also possible to drive only the desired one or more of micro-blowers 230, 232, . . . , 250 or 252 or micro-blowers 260, 262, . . . , 268 or 270 without driving sirocco fan 100. Further, it is also possible to drive sirocco fan 100 only, without driving any of micro-blowers 230, 232, . . . , 250 and 252 and micro-blowers 260, 262, . . . , 268 and 270.

More specifically, referring to FIG. 7, when a scent is to be emitted from aroma cartridge 180 belonging to the outer group, for example, control circuit board 104 applies AC voltage to a piezoelectric element in micro-blower 230 that corresponds to aroma cartridge 180. In response to this AC voltage, the piezoelectric element in micro-blower 230 oscillates, to vibrate a thin plate to which the piezoelectric element is adhered, causing an air flow. The air is introduced to the inside of aroma cartridge 180 from the nozzle of micro-blower 230 through air-feeding inlet 225 (see FIG. 4) of aroma cartridge 180. As a result, pressure in aroma cartridge 180 temporarily increases and, in response to this increased pressure, aroma cartridge 180 emits scented air from the scent source sealed inside to the outside through scent-emitting opening 224.

Figure 21:
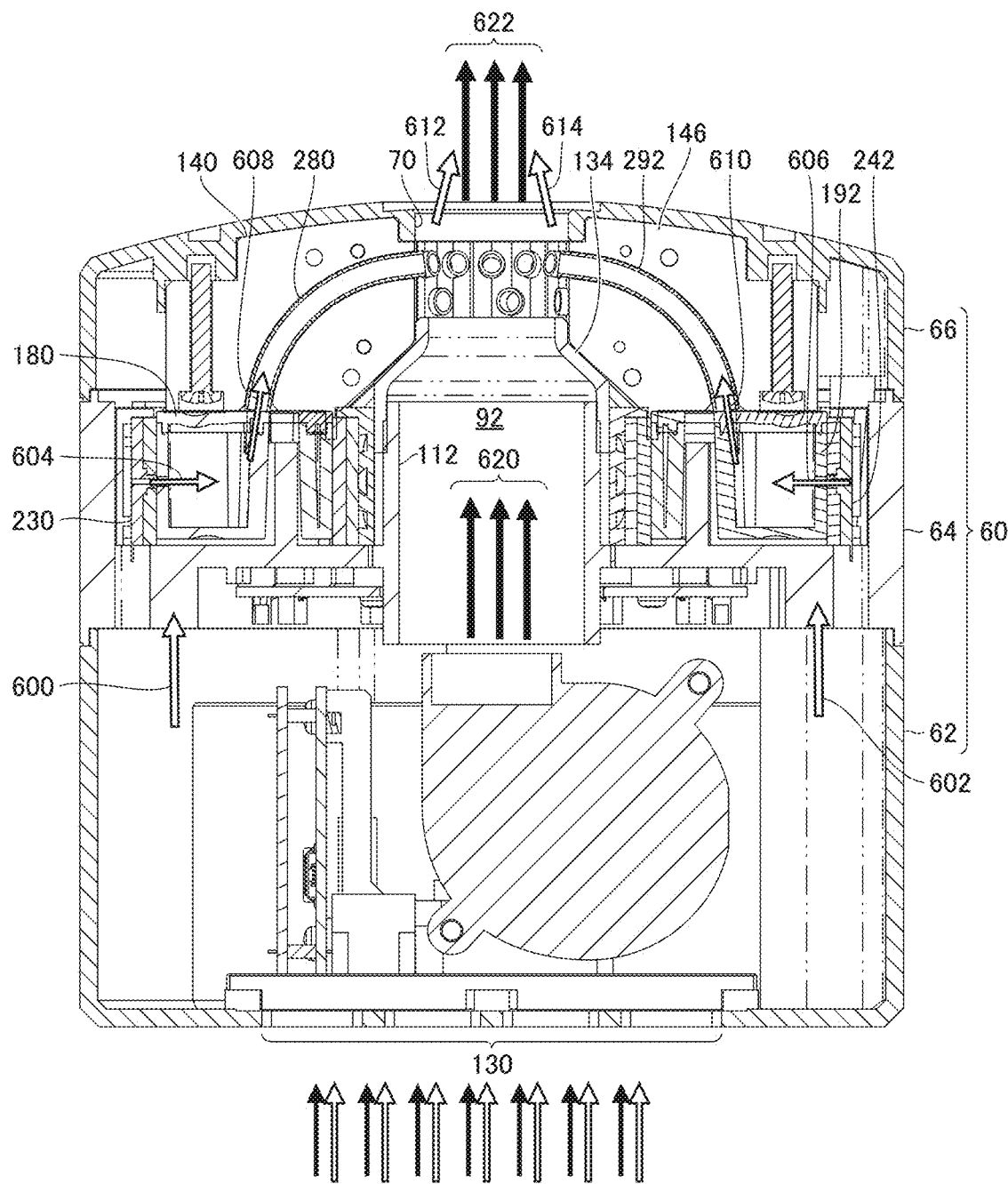
FIG. 21 is a cross-sectional view of the aroma display taken along the line 7-7 in FIG. 1, showing an example of air route in the aroma display shown in FIG. 1.

Particularly referring to FIG. 21, at this time, the air used by micro-blower 230 enters to housing 60 through openings 130 formed at the bottom surface of base housing 62 and passes through an air passage 600 to the position of micro-blower 230. The air is further drawn into micro-blower 230, passes through air passage 604 including the nozzle of micro-blower 230 and air-feeding inlet 225 (see FIG. 4) of aroma cartridge 180 and intermittently introduced to the inside of aroma cartridge 180. The pressure in the hollow portion in aroma cartridge 180 temporarily increases repeatedly in response to the introduction of the air. In response to the heightened pressure, scented air from the scent source sealed in the hollow portion of aroma cartridge 180 is emitted through scent-emitting opening 224 (see FIG. 4) of aroma cartridge 180. The emitted scented air 608 enters tube 80 via one end of tube 80, is guided to the side of nozzle 134 by tube 280, and is emitted as scented air 612 from the other end of tube 280 into opening 70.

Emission of the scented air 612 is repeated as long as the AC voltage is applied to micro-blower 230. When application of AC voltage to micro-blower 230 ends, micro-blower 230 stops operation and feeding of air to aroma cartridge 180 stops. As a result, emission of scented air from aroma cartridge 180 stops. Therefore, by controlling the start and stop timing of AC voltage application to micro-blower 230, it is possible to emit a desired scent from aroma display 50 at a desired timing for a desired time period.

Here, if sirocco fan 100 is operating, an air flow 620 generated by sirocco fan 100 enters from air passage 92 in duct member 112 to the inside of nozzle 134, accelerated therein as the inner diameter of nozzle 134 becomes narrower at the upper side, and emitted as emission air 622 to the outside of aroma display 50. At this time, scented air 612 is drawn into emission air 622 and carried far by emission air 622. If sirocco fan 100 is not operating, scented air 612 is emitted only in the vicinity of aroma display 50 and if there is no other wind, it stays there. If sirocco fan 100 is operated thereafter, the scent lingering around aroma display 50 is dissipated.

The operation is the same for other aroma cartridges of the outer group, such as aroma cartridge 192. The air taken in from opening 130 passes through air passage 602 and drawn into micro-blower 242 of aroma cartridge 192, and introduced to the inside of aroma cartridge 192. As a result, scented air 610 is guided through tube 292 to the side of nozzle 134, and emitted to the inside of opening 70 as scented air 614 from the other end of tube 292. The flow of scented air thereafter is the same as in the case of aroma cartridge 180.

Figure 22:
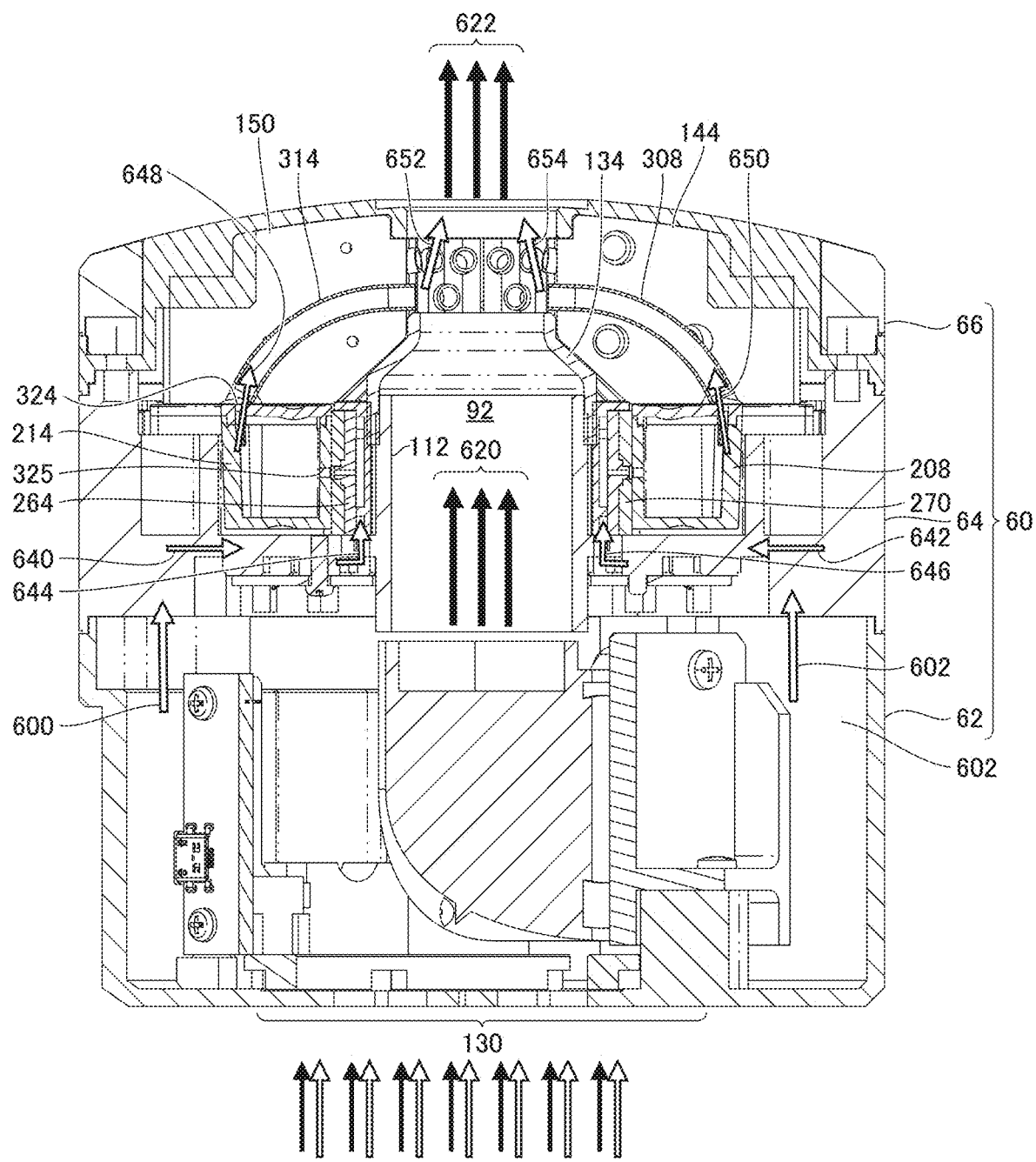
FIG. 22 is a cross-sectional view of the aroma display taken along the line 9-9 in FIG. 1, showing another example of air route in the aroma display shown in FIG. 1.

When scented air is to be emitted from an aroma cartridge of the inner group, for example, from aroma cartridge 214, aroma display 50 operates in the following manner. Referring to FIG. 22, AC voltage is applied to micro-blower 264 arranged between aroma cartridge 214 and duct member 112. In response to the AC voltage, micro-blower 264 takes in the air that is taken in through opening 130 to housing 60, through air passages 600, 640 and 644 and intermittently introduces the air to the inside of aroma cartridge 214, in the similar manner as micro-blower 230 shown in FIG. 21. As a result, the inner pressure of aroma cartridge 214 temporarily increases repeatedly. In response to the increased pressure, scented air from the scent source sealed in aroma cartridge 214 is emitted from scent-emitting opening 324.

The scented air 648 is introduced to the inside of tube 314 from one end of tube 314, guided by tube 314 toward nozzle 134, and emitted as scented air 652 from the other end of tube 314 to the inside of opening 70. The operation thereafter of aroma display 50 is the same as when an aroma cartridge of the outer group is operated. Therefore, description thereof will not be repeated here.

The operation of aroma cartridge 208 of the inner group arranged opposite to aroma cartridge 214 with duct member 112 in between in FIG. 22 is also the same. By driving micro-blower 270, scented air 650 is emitted from cartridge 208 through tube 308 to the inside of opening 70, as scented air 654. The operation of aroma display 50 thereafter is the same as when an aroma cartridge of the outer group is operated or when aroma cartridge 214 is operated. Therefore, description thereof will not be repeated here.

As described above, according to the present embodiment, it is possible to load a large number of aroma cartridges in aroma display 50 and to emit scented air from any of the aroma cartridges. These aroma cartridges have the same shape and same structure and those belonging to the outer group are not distinguished from those belonging to the inner group. Therefore, any aroma cartridge that is of the same type as used in an already commercially available aroma display can be used. By dividing the aroma cartridges to inner and outer groups, housing space is effectively used to allow use of a large number of aroma cartridges while preventing increase in size of the housing. As a result, an aroma display that can emit a desired scent or scents using a large number of aroma cartridges can be provided, while preventing increase in size, not necessitating use of a special aroma cartridge by using common aroma cartridges.

Since the inner wall of tubes 280 etc. is coated with fluororesin, scented air emitted, for example, from aroma cartridge 180 is efficiently guided toward nozzle 134 and emitted. After emission from aroma cartridge 180 stops, scent components hardly adhere to the inner wall of tube 280. Therefore, when aroma cartridge 180 is switched to another aroma cartridge, the possibility of undesirable blending of scents hardly exists. Even when any scent component remains inside tube 280, the lingering scent is immediately discharged from tube 280 when aroma display 50 is operated the next time. Therefore, when aroma cartridge 180 is stopped and a scent is emitted from another aroma cartridge, lingering scent hardly poses any problem.

Further, even when any scent adheres to the inside of, for example, tube 280 by the use of aroma display 50 for a long time, any tube can be exchanged to a new one by removing and decoupling tube fixing 140 or the like from cap 66. Therefore, any scent adhered inside the tube does not pose any problem and a desired scent or scents can always be generated effectively. Further, eighteen aroma cartridges are accommodated in aroma-cartridge-accommodating housing 64, divided to the outer group of twelve cartridges and the inner group of six cartridges. Therefore, a user can advantageously use the aroma cartridges of the outer group and the aroma cartridges of the inner group distinguished from each other. By way of example, it is possible for the user to load aroma cartridges of floral scents in the inner group and aroma cartridges other than the floral scents such as coffee or mint in the outer group, so that exchange of aroma cartridges becomes easier.

Second Embodiment

The aroma display according to the above-described first embodiment allows use of at most twelve aroma cartridges as the outer group and at most six cartridges as the inner group. Specifically, the ratio of the number of aroma cartridges belonging to the outer group to the number of those belonging to the inner group is 2:1. The present invention, however, is not limited to such an embodiment. The ratio may not be 2:1.

Figure 23:
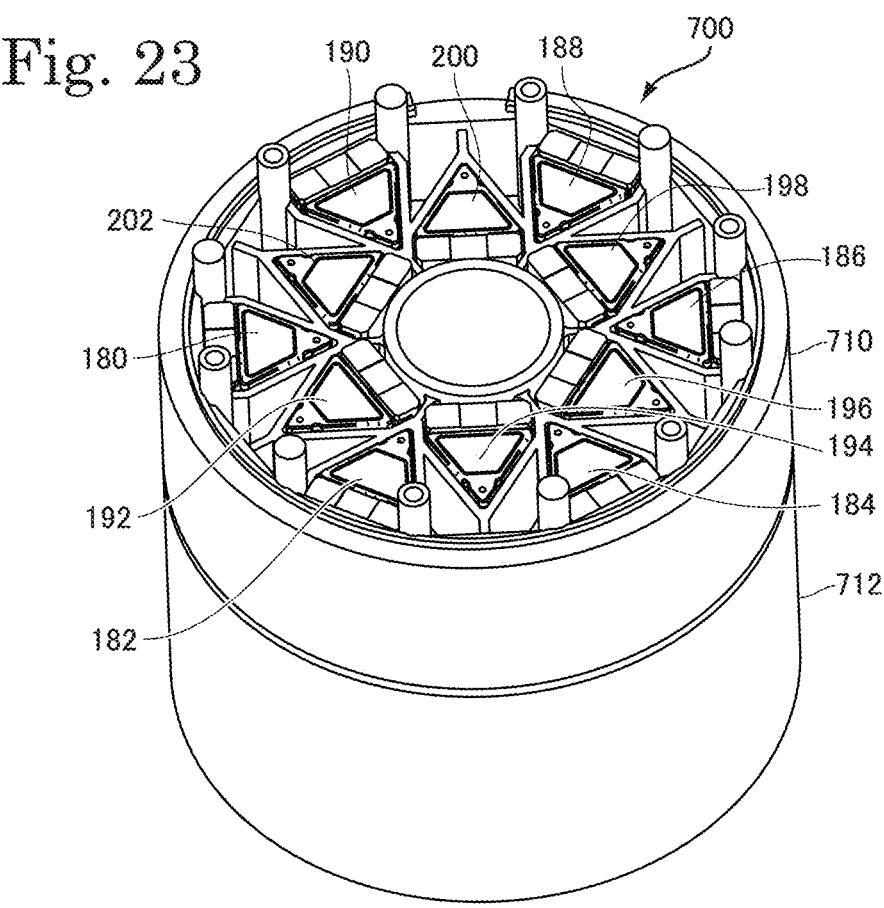
FIG. 23 is a perspective view of the aroma display's aroma-cartridge-accommodating housing and the base housing when the cap is removed, in accordance with a second embodiment of the present invention.
Figure 24:
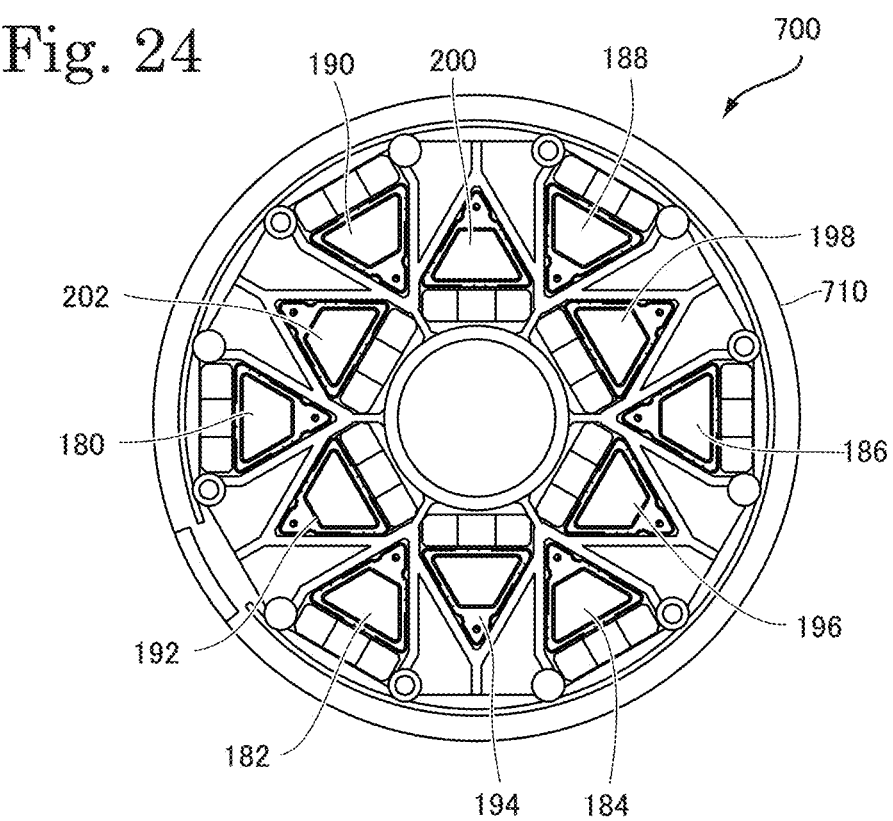
FIG. 24 is a plan view of the aroma-cartridge-accommodating housing shown in FIG. 23.

FIGS. 23 and 24 show a perspective view of an aroma-cartridge-accommodating housing 710 and a base housing 712 and a plan view of the aroma-cartridge-accommodating housing 710 of the aroma display 700 in accordance with a second embodiment. Referring to FIGS. 23 and 24, aroma-cartridge-accommodating housing 710 has a cartridge-loading section to which twelve aroma cartridges 180, 182, . . . , 200 and 202 can be loaded. The cartridge-loading section includes an outer cartridge-loading section for loading six outer cartridges 180, . . . , 190 and an inner cartridge-loading section for loading six inner cartridges 192, . . . , 202. These cartridges 180, . . . , 202 are the same as those used in the first embodiment.

Six aroma cartridges 180, . . . , 190 loaded to the outer cartridge-loading section are arranged at six positions of rotation symmetry about the central axis of aroma-cartridge-accommodating housing 710 such that the scent-emitting opening of each cartridge faces the direction of the central axis of aroma-cartridge-accommodating housing 710 and the air-feeding inlet faces the outer circumference of aroma-cartridge-accommodating housing 710. Six aroma cartridges 192, . . . , 202 loaded to the inner cartridge-loading section are arranged at six positions of rotation symmetry about the central axis of aroma-cartridge-accommodating housing 710 such that the scent-emitting opening of each cartridge faces the outer circumference of aroma-cartridge-accommodating housing 710 and the air-feeding inlet faces the direction of the central axis of aroma-cartridge-accommodating housing 710. At the portion of air-feeding inlet of each of these aroma cartridges 180, . . . 202, a micro-blower is provided for introducing air to the aroma cartridge.

Aroma display 700 includes a cap (not shown) similar to the cap 66 shown in FIGS. 1 to 3 and 17 of the first embodiment, for covering aroma-cartridge-accommodating housing 710. On that surface of the cap which faces aroma-cartridge-accommodating housing 710, tubes (not shown) for guiding scents to the central opening (similar to opening 70 of FIG. 1) from scent-emitting openings of aroma cartridges 180, . . . , 202 are fixed by tube fixings (not shown) such as tube fixing 140 (see FIG. 17) of the first embodiment.

Other portions of aroma-cartridge-accommodating housing 710 in accordance with the second embodiment are the same as those of aroma display 50 in accordance with the first embodiment.

Different from aroma display 50 in accordance with the first embodiment, aroma display 700 in accordance with the second embodiment can accommodate only twelve aroma cartridges in aroma-cartridge-accommodating housing 710. It is advantageous, however, since the diameter of aroma-cartridge-accommodating housing 710 can be made smaller and more compact as compared with the first embodiment.

Further, since twelve aroma cartridges are divided between the inner and outer groups, this embodiment achieves the same effect as the first embodiment in that the user can distinguish and use aroma cartridges to be loaded in the outer group and those to be loaded to the inner group.

The aroma display according to the above-described first embodiment allows use of at most twelve aroma cartridges as the outer group and at most six cartridges as the inner group. The aroma display according to the second embodiment allows use of at most six cartridges both in the inner and outer groups. The present invention, however, is not limited to such embodiments. The numbers of aroma cartridges belonging to the inner and outer groups may be different from those mentioned above. It is unnecessary that the number of aroma cartridges belonging to the two groups have a common divisor. By way of example, five aroma cartridges may be loadable as the inner group and fourteen aroma cartridges may be loadable as the outer group. From the viewpoint of effectively making use of the space in housing 60, however, it is preferable that the number of aroma cartridges belonging to the outer group is larger than the number of aroma cartridges belonging to the inner group, and in order to effectively utilize the space between adjacent aroma cartridges, it is desirable that two numbers have a common divisor.

Further, in order to fix tubes corresponding to respective aroma cartridges to cap 66 by means of a tube fixing such as tube fixing 140, it is desirable that a plurality of tubes can be fixed on one tube fixing. In that case, to use tube fixings of the same structure, it is desirable that the tubes fixed by the tube fixing have the same configuration. Specifically, it is desirable that each tube fixing fixes a prescribed number of tubes for the outer group aroma cartridges and a prescribed number of tubes for the inner group aroma cartridges. Therefore, it is desired that the sum total of aroma cartridges of the outer group and the sum total of aroma cartridges of the inner group are M:N (where M, N are natural numbers satisfying the relation M≥N, preferably, relatively prime natural numbers satisfying the relation M>N). Here, if each tube fixing is adopted to fix M tubes for the outer group and N tubes for the inner group collectively on cap 66, every tube fixing can have the same structure. In the first embodiment, M=2 and N=1, and in the second embodiment, M=N=1. It goes without saying that tubes of multiples of these numbers may be fixed by each tube fixing.

Further, in the first and second embodiments, a micro-blower implemented by a piezoelectric element is used for emitting scent components from each aroma cartridge. The present invention, however, is not limited to such embodiments. In place of the micro-blower, a small fan may be used. Further, in the embodiments above, a sirocco fan is used for generating a scent-free air flow. The present invention, however, is not limited to such embodiments, and a different type fan may be used. By way of example, a fan using a propeller or a turbo fan may be used.

Further, in the first embodiment above, the tubes for aroma cartridges belonging to the outer group are opened at equal distances on a circle on a plane perpendicular to the central axis (therefore, the central axis of opening 70 and housing 60) of nozzle 134, on the side wall of nozzle 134. Similarly, the tubes for aroma cartridges belonging to the inner group are also opened at equal distances on a circle on a plane perpendicular to the central axis of nozzle 134 on the side wall of nozzle 134. The plane on which the openings of the outer group tubes are positioned is different from the plane on which the openings of the inner group tubes are positioned. By this arrangement, even when it is difficult to position openings of all tubes for all aroma cartridges on one circle of one plane on the sidewall of nozzle 134, it is possible to effectively ensure positions for forming openings. Further, thanks to this arrangement, from any aroma cartridge belonging to the same group, scent can be emitted under the same conditions. The present invention, however, is not limited to such embodiments. The tube openings may be all positioned on one plane, if it is possible to arrange all openings of the tubes on the sidewall of nozzle 134. If the sidewall of nozzle 134 has a short circumferential length and the number of aroma cartridges is large, cartridge openings may be positioned on three or more planes.

Further, in the embodiments above, every tube for the aroma cartridge belonging to any group is positioned in nozzle 134. The present invention, however, is not limited to such embodiments. By way of example, end portions for emitting scented air for a group or all groups may be arranged on a surface of cap 66 near the opening 70 inside opening area 68 shown in FIG. 1.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

What is claimed is:

1. An aroma display for emitting scented air from a desired one of a plurality of aroma cartridges each having a scent source sealed therein, comprising:
   an aroma-cartridge-accommodating housing for accommodating said plurality of aroma cartridges around a first axis; and
   a cap attached to said aroma-cartridge-accommodating housing to cover said aroma-cartridge-accommodating housing, having an opening through which the scented air is emitted; wherein
   each of said plurality of aroma cartridges has a housing with a hollow portion and a first surface, and a scent source sealed in the hollow portion, the housing having an air-feeding inlet for feeding air to said hollow portion, and a scent-emitting opening for emitting scented air from said scent source to the outside of the housing in response to increase of pressure in said hollow portion caused by the air fed from said air-feeding inlet, said scent-emitting opening formed at a position on said first surface off of a geometrical center of said first surface;
   said aroma display further comprising:
   an air-feeding mechanism for individually feeding air to said air-feeding inlet of said plurality of aroma cartridges; wherein
   said aroma-cartridge-accommodating housing includes a first cartridge-loading section allowing loading of a first group of aroma cartridges consisting of a first number of aroma cartridges and a second cartridge-loading section allowing loading of a second group of aroma cartridges consisting of a second number of aroma cartridges, the second number being equal to or smaller than the first number;
   said first cartridge-loading section allows loading of the aroma cartridges of the first group such that a distance between the geometrical center of said first surface of each aroma cartridge of the first group and said first axis becomes a first distance;
   said second cartridge-loading section allows loading of the aroma cartridges of the second group such that a distance between the geometrical center of said first surface of each aroma cartridge of the second group and said first axis becomes a second distance smaller than the first distance;

the aroma display further comprises a plurality of tubes respectively connecting said scent-emitting openings of said plurality of aroma cartridges and said opening of said cap;

among said plurality of tubes, each of said tubes of a first group corresponding to the aroma cartridges of said first group has a first end in contact with said scent-emitting opening of the aroma cartridge and a second end opened in said opening of said cap; and said cap holds said tubes of said first group such that each of said second ends of said tubes of the first group is positioned on a first circle on a plane perpendicular to said first axis.

2. The aroma display according to claim 1, further comprising an air-emitting mechanism provided on a side opposite to said cap with respect to said aroma-cartridge-accommodating housing, for feeding scent-free air to said opening of said cap.

3. The aroma display according to claim 2, further comprising a duct member provided passing through the central portion of said aroma-cartridge-accommodating housing to surround said first axis, for guiding wind fed from said air-emitting mechanism to said opening of said cap; wherein said cap includes a nozzle having a bottom portion in contact with an end portion on the side of said cap of said duct member and a tip end portion of a smaller area than said bottom portion, defining circumference of said opening; and said second end of each of said plurality of tubes opens to the inside of a space defined by said nozzle.

4. The aroma display according to claim 1, wherein among said plurality of tubes, each of said tubes of a second group corresponding to the aroma cartridges of said second group has a first end in contact with said scent-emitting opening of the aroma cartridge and a second end opened in said opening of said cap; and said cap holds said tubes of said second group such that each of said second ends of said tubes of the second group is positioned on a second circle on a plane perpendicular to said first axis.

5. The aroma display according to claim 4, further comprising an air-emitting mechanism provided on a side opposite to said cap with respect to said aroma-cartridge-accommodating housing, for feeding scent-free air to said opening of said cap.

6. The aroma display according to claim 5, further comprising a duct member provided passing through the central portion of said aroma-cartridge-accommodating housing to surround said first axis, for guiding wind fed from said air-emitting mechanism to said opening of said cap; wherein said cap includes a nozzle having a bottom portion in contact with an end portion on the side of said cap of said duct member and a tip end portion of a smaller area than said bottom portion, defining circumference of said opening; and said second end of each of said plurality of tubes opens to the inside of a space defined by said nozzle.

7. The aroma display according to claim 4, wherein ratio of the number of aroma cartridges of said first group to the number of aroma cartridges of said second group is M:N (where M, N are relatively prime natural numbers satisfying the relation M>N); and said cap includes a cover member having an end portion fixed on a circumferential wall at an end portion of said aroma-cartridge-accommodating housing on the side of said cap and said opening formed at the center, and having a shape gradually tapered upward from said end portion to said opening, and a plurality of tube fixings each for detachably fixing M said tubes of the first group and N said tubes of the second group on a surface of said cover member on the side of said aroma-cartridge-accommodating housing.

8. The aroma display according to claim 7, further comprising an air-emitting mechanism provided on a side opposite to said cap with respect to said aroma-cartridge-accommodating housing, for feeding scent-free air to said opening of said cap.

9. The aroma display according to claim 8, further comprising a duct member provided passing through the central portion of said aroma-cartridge-accommodating housing to surround said first axis, for guiding wind fed from said air-emitting mechanism to said opening of said cap; wherein said cap includes a nozzle having a bottom portion in contact with an end portion on the side of said cap of said duct member and a tip end portion of a smaller area than said bottom portion, defining circumference of said opening; and said second end of each of said plurality of tubes opens to the inside of a space defined by said nozzle.

10. The aroma display according to claim 1, wherein said housing of said plurality of aroma cartridges has a triangular prism shape, and said first surface is an upper surface of said triangular prism.

11. The aroma display according to claim 2, wherein said housing of said plurality of aroma cartridges has a triangular prism shape, and said first surface is an upper surface of said triangular prism.

12. The aroma display according to claim 4, wherein said housing of said plurality of aroma cartridges has a triangular prism shape, and said first surface is an upper surface of said triangular prism.

* * * * *